(12) United States Patent
Kim et al.

(10) Patent No.: US 7,795,361 B2
(45) Date of Patent: *Sep. 14, 2010

(54) PHOTOREACTIVE POLYMER AND PROCESS OF MAKING THE SAME

(75) Inventors: Heon Kim, Yeosu (KR); Sung Ho Chun, Daejeon (KR); Keon Woo Lee, Daejeon (KR); Sung Joon Oh, Daejeon (KR); Kyungjun Kim, Daejeon (KR); Jungho Jo, Suwon (KR); Byung Hyun Lee, Daejeon (KR); Min Young Lim, Seongnam (KR); Hye Won Jeong, Daejeon (KR)

(73) Assignee: LG Chem, Ltd., Seoul (KR)

( * ) Notice: Subject to any disclaimer, the term of this patent is extended or adjusted under 35 U.S.C. 154(b) by 1232 days.

This patent is subject to a terminal disclaimer.

(21) Appl. No.: 11/325,414

(22) Filed: Jan. 5, 2006

(65) Prior Publication Data

US 2006/0160970 A1 Jul. 20, 2006

(30) Foreign Application Priority Data

| Jan. 5, 2005 | (KR) | .................. 10-2005-0000833 |
| Jan. 4, 2006 | (KR) | .................. 10-2006-0001087 |

(51) Int. Cl.
*C08G 61/06* (2006.01)
*C08F 32/08* (2006.01)
*C08F 4/80* (2006.01)
*C07C 13/42* (2006.01)

(52) U.S. Cl. .............. 526/282; 526/117; 526/134; 526/139; 526/160; 526/161; 526/256; 526/262; 526/332

(58) Field of Classification Search .......... 526/282, 526/256, 262, 332, 117, 134, 139, 160, 161
See application file for complete search history.

(56) References Cited

U.S. PATENT DOCUMENTS

| 3,187,018 | A * | 6/1965 | Tinsley et al. .......... 549/545 |
| 5,464,669 | A | 11/1995 | Kang et al. |
| 5,552,504 | A | 9/1996 | Bennett et al. |
| 6,169,152 | B1 | 1/2001 | Sakai |
| 6,946,523 | B2 * | 9/2005 | Dershem et al. .......... 525/216 |
| 7,541,073 | B2 * | 6/2009 | Kim et al. .................. 428/1.2 |
| 2001/0003772 | A1 | 6/2001 | Hatakeyama et al. |
| 2002/0146638 | A1 | 10/2002 | Ito et al. |
| 2003/0118933 | A1 | 6/2003 | Han et al. |

FOREIGN PATENT DOCUMENTS

| EP | 1 096 317 A1 | 5/2001 |
| EP | 1 096 318 | 5/2001 |
| EP | 0298408 | 8/2001 |
| EP | 1127870 | 11/2003 |
| JP | 61-292601 | 12/1986 |
| JP | 10-087859 | 4/1998 |
| JP | 11-181127 | 7/1999 |
| KR | 10-2005-0033565 | 4/2004 |
| TW | 523637 | 3/2003 |
| TW | 200426440 | 12/2004 |

OTHER PUBLICATIONS

Hreha, et al, "Synthesis of acrylate and norbornene polymers with pendant 2,7-bis(diarylamino)fluorene hole-transport groups," Tetrahedron, 60 (2004) 7169-7176.*

Dyaduysha,et al. "*Peculiarity of an Oblique Liquid Crystal Alignment Induced By A Photosensitive Orientant*"; Japanese Journal of Applied Physics, vol. 34 (1995) pp. L1000-L1002 Part 2, No. 8A, (Aug. 2005).

Schadt, et al. "*Surface-Induced Parallel Alignment of Liquid Crystals by Linearly Polymerized Photopolymers*" Japanese Journal of Applied Physics, vol. 31(1992) pp. 2155-2164 Part 1, No. 7,(Jul. 1992).

* cited by examiner

*Primary Examiner*—Fred M Teskin
(74) *Attorney, Agent, or Firm*—McKenna Long & Aldridge LLP

(57) ABSTRACT

Provided are a photoreactive polymer that includes a multi-cyclicmulticyclic compound at as its main chain and a method of preparing the same. The photoreactive polymer exhibits excellent thermal stability since it includes a multi-cyclic-multicyclic compound having a high glass transition temperature at as its main chain. In addition, the photoreactive polymer has a relatively large vacancy so that a photoreactive group can move relatively freely in the main chain therein. As a result, a slow photoreaction rate, which is a disadvantage of a conventional polymer material used to form an alignment layer for a liquid crystal display device, can be overcome.

18 Claims, 2 Drawing Sheets

PHOTOREACTIVE POLYMER AND PROCESS OF MAKING THE SAME

CROSS-REFERENCE TO RELATED PATENT APPLICATIONS

This application claims the benefit of Korean Patent Application Nos. 10-2005-0000833, filed on Jan. 5, 2005, and 10-2006-0001087, filed on Jan. 4, 2006, in the Korean Intellectual Property Office, the disclosures of which are incorporated herein in their entirety by reference.

BACKGROUND OF THE INVENTION

1. Field of the Invention

The present invention relates to a photoreactive polymer, and more particularly, to a photoreactive polymer that has an orientation due to photoreaction, and is thermally stable due to a multi-cyclic multicyclic compound contained therein at as its main chain, and quickly responds to light.

2. Description of the Related Art

Liquid crystal displays (LCDs) are regarded as most competitive displays to be able to for replace replacing cathode-ray tubes since they are lightweight and have a low power consumption power. In particular, thin film transistor-liquid crystal displays (TFT-LCDs) operating by TFTs, which operate using a TFT, exhibit a very quick responding speed because respective pixels operate independently, so that high quality moving images can be realized. Therefore, TFT-LCDs have a wide range of applications, such as notebook computers, wall mount TVs, and the like.

According to a conventional method of manufacturing a color TFT-LCD, a TFT driving device and an ITO transparent electrode are deposited on a glass substrate and then an alignment layer is deposited thereon, thus forming a lower substrate. A spacer formed of sealant is interposed between upper and lower substrates to form a space into which a liquid crystal material is to be injected. A polarized film covers external surface of the glass substrate, and finally, a the liquid crystal material is injected into the space formed between the substrates and hardened to manufacture an LCD cell.

In order to use liquid crystals as an optic switch in a TFT-LCD, liquid crystals needs to be initially oriented in a predetermined direction on a TFT, which is disposed in the most inner portion of a display cell. For this purpose, a liquid crystal alignment film is used.

An alignment layer can be formed by rubbing a polymer resin film, such as a polyimide resin, formed on a substrate using a cloth or the like in a predetermined direction. Alternatively, an alignment layer can be formed by obliquely depositing $SiO_2$. The rubbing treatment is disadvantageous in that impurities may be generated by the contacting, a production yield may decrease due to static electricity, and a contrast may decrease. The obliquely depositing method is not suitable for forming a large display screen and is expensive. Accordingly, the obliquely depositing method is not suitable for a large-size liquid crystal display device.

In order to solve these problems, a non-rubbing process using a photopolymerizable alignment material has been developed. In the non-rubbing process, liquid crystals are aligned by photopolymerisation resulting from optical irradiation. The non-rubbing process is disclosed by M. Schadt et al. (Jpn. J. Appl. Phys., Vol 31, 1992, 2155), Dae S. Kang et al. (U.S. Pat. No. 5,464,669), and Yuriy Reznikov (Jpn. J. Appl. Phys. Vol. 34, 1995, L1000). Photoalignment refers to a mechanism for aligning of liquid crystals in which a photoreactive group bound to a polymer reacts when exposed to prepolarized ultraviolet rays such that a main chain of the polymer is aligned in a predetermined direction.

A pPhotopolymerizable alignment layer is typically formed of a polycinnamate-based polymer, such as poly(vinyl cinnamate) PVCN and poly(vinyl methoxycinnamate) PVMC. Although the polycinnamate-based polymer has excellent photoalignment characteristics, it is thermally unstable. That is, thermal stability of the alignment layer is dependent on the thermal stability of a polymer used to form the alignment layer and the main chain of a PVCN-based polymer has a glass transition temperature of 100° C. or less. Therefore, the thermal stability of the alignment layer is low.

Meanwhile, Japanese Laid-open Publication No. hei 11~181127 teaches a method of forming an alignment layer formed of a polymer that containing contains acrylate, metacrylate as a main chain and a photoreactive group, such as a cinnamic acid group, as a side chain and an alignment layer formed using the method. In this case, since a polymer has a low mobility, sufficient alignment characteristics cannot be obtained even when the polymer is exposed to light for a long time. This which is because the photoreactive group contained in the polymer is bound to the main chain of the polymer and cannot react quickly when exposed to a polarized light. Accordingly, a long period of time is required to produce a network polymer and thus process efficiency decreases. In addition, when the alignment treatment is completed for an insufficient time not performed for a sufficient length of time, the produced liquid crystal display device has insufficiently aligned liquid crystals and a low dichroic ratio, and a contrast thereof deteriorates.

Accordingly, there is an increasing need to develop a photoreactive polymer having an excellent thermal stability and an improved photoreaction rate.

SUMMARY OF THE INVENTION

The present invention provides a compound that can be used as a monomer of a polymer having an excellent thermal stability and an improved photoreaction rate.

The present invention also provides a polymer of the compound.

The present invention also provides a method of preparing the polymer.

According to an aspect of the present invention, there is provided a multi-cyclic multicyclic compound that has a photoactive group at as its main chain.

According to another aspect of the present invention, there is provided a polymer including a repeat unit induced from the multicyclic compound.

According to yet yet another aspect of the present invention, there is provided a method of polymerizing a polymer including the multicylcic compound as a monomer at a temperature of 10° C. to 200° C. in the presence of a catalyst mixture including: a procatalyst containing a Group 10 transition metal; and a cocatalyst capable of weakly coordinately bonding to the transition metal of the procatalyst.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
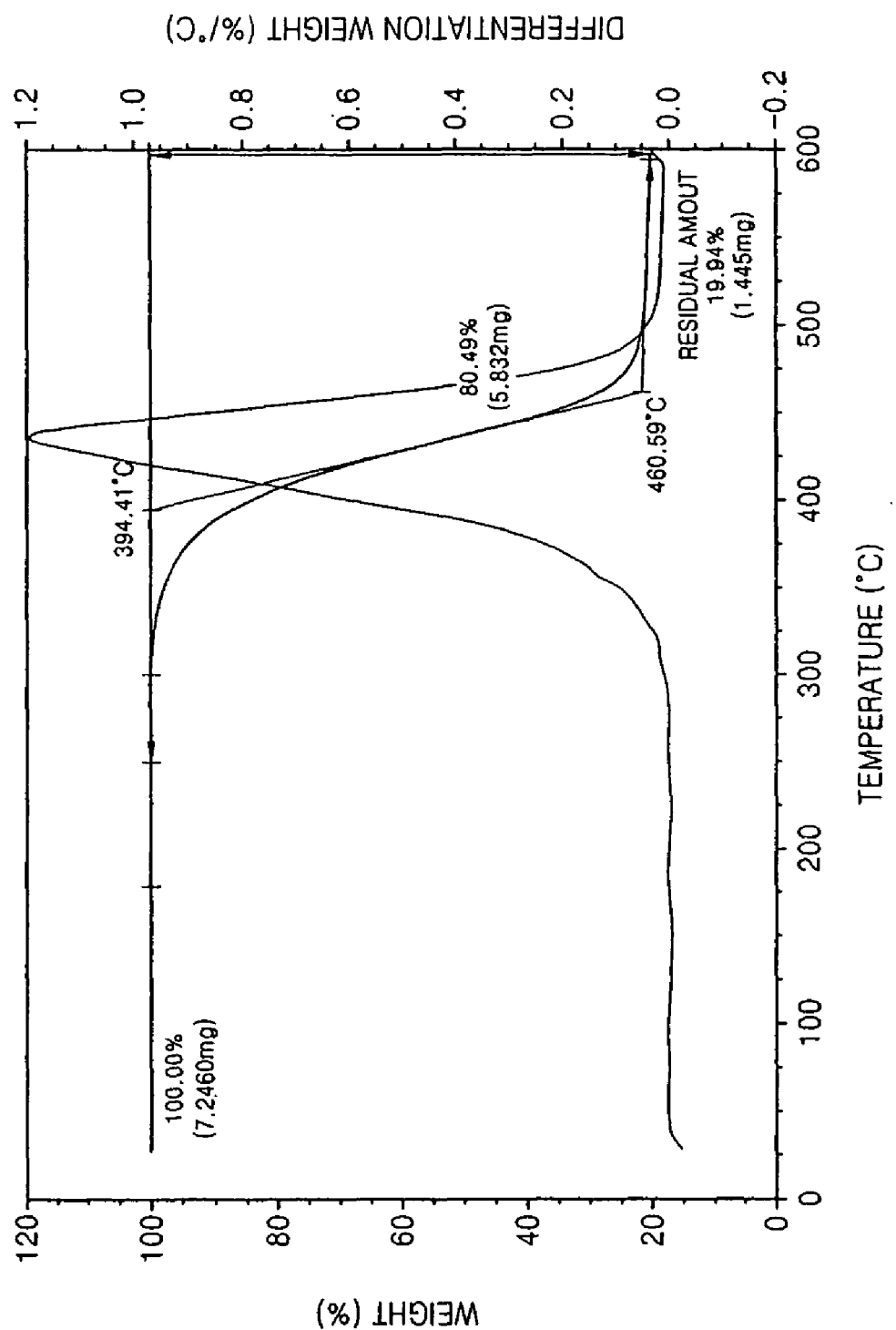
FIG. 1 shows thermogravimetric analysis curves of a polymer according to an Example 3.

A multi-cyclicmulticyclic compound polymer including a photoactive group according to an embodiment of the present invention has a high glass transition temperature and excellent thermal stability because it includes a multi-cyclicmulticyclic compound at as its main chain. The polymer has a relatively large vacancy so that a photoreactive group moves relatively freely, thus having a high photoreaction rate. Therefore, the use of the polymer according to an embodiment of the present invention overcomes a conventional problem, that is, a low photoreaction rate occurring when an alignment film of a liquid display device is formed of a conventional polymer material.

The multi-cyclicmulticyclic compound including a the photoactive group used to form a liquid crystal alignment layer according to an the current embodiment of the present invention is represented by formula 1:

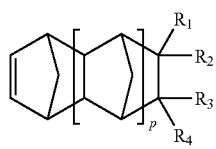

(1)

where p is an integer of 0 to 4;

at least one of $R_1$, $R_2$, $R_3$, and $R_4$ is a radical selected from the a group consisting of a compound represented by formula 1a, a compound represented by formula 1b, a compound represented by formula 1c, and a compound represented by formula 1 d; and the rest of remaining three of $R_1$, $R_2$, $R_3$, and $R_4$ is are each independently hydrogen, halogen, a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, a substituted or unsubstituted C2-C20 alkynyl group, or a polar group selected from non-hydrocarbonaceous polar groups containing at least one of oxygen, nitrogen, phosphor, sulfur, silicon, and boron, wherein when none of $R_1$, $R_2$, $R_3$, and $R_4$ is hydrogen, halogen, or the non-hydrocarbonaceous polar group, R, is connected to $R_2$ or $R_3$ is connected to $R_4$ to form a C1-C10 alkylidene group, or $R_1$ or $R_2$ is connected to one of $R_3$ and $R_4$ to form a C4-C12 saturated or unsaturated cyclic group or a C6-C24 aromatic cyclic compound, the non-hydrocarbonaceous polar group is selected from the a group consisting of —$OR_6$, —$OC(O)OR_6$, —$R_5OR_6$, —$R_5OC(O)OR_6$, —$C(O)OR_6$, —$R_5C(O)OR_6$, —$C(O)R_6$, —$R_5C(O)R_6$, —$OC(O)R_6$, —$R_5OC(O)R_6$, —$(R_{50})_p$—$OR_6$, —$(OR_5)_p$—$OR_6$, —$C(O)$—$O$—$C(O)R_6$, —$R_5C(O)$—$O$—$C(O)R_6$, —$SR_6$, —$R_5SR_6$, —$SSR_6$, —$R_5SSR_6$, —$S(=O)R_6$, —$R_5S(=O)R_6$, —$R_5C(=S)R_6$, —$R_5C(=S)SR_6$, —$R_5SO_3R_6$, —$SO_3R_6$, —$R_5N=C=S$, —$NCO$, $R_5$—$NCO$, —$CN$, —$R_5CN$, —$NNC(=S)R_6$, —$R_5NNC(=S)R_6$, —$NO_2$, —$R_5NO_2$,

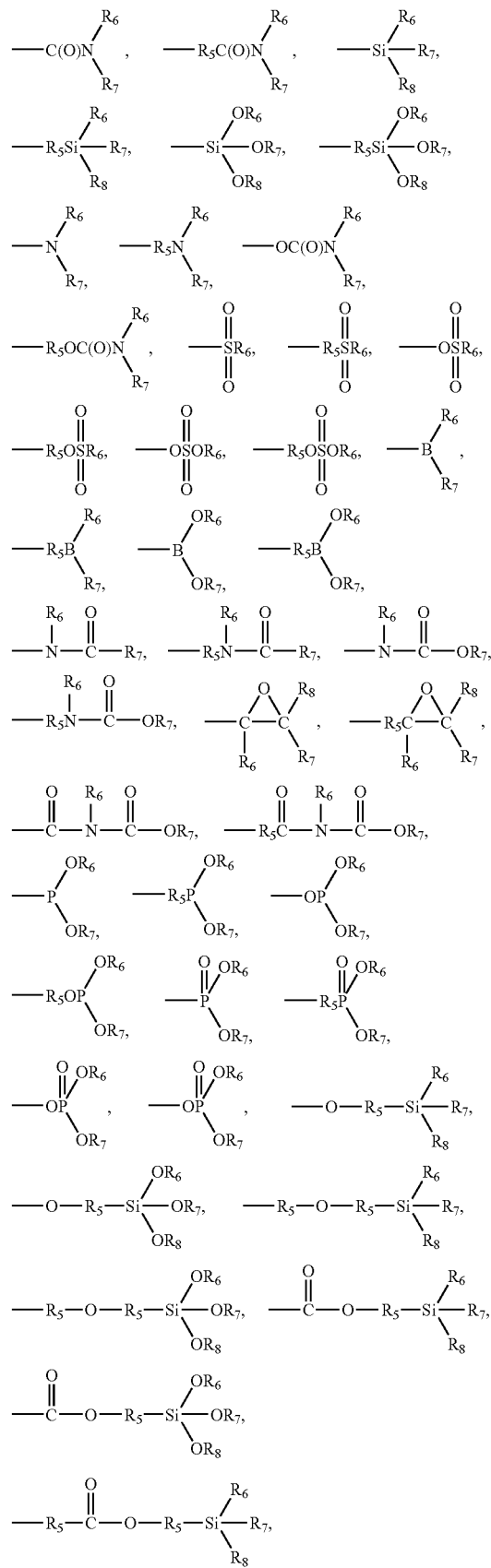

-continued

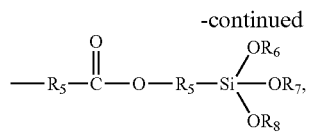
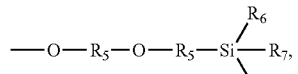
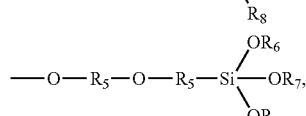
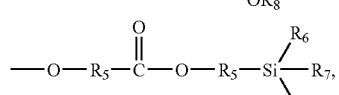
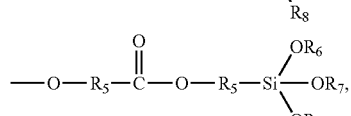
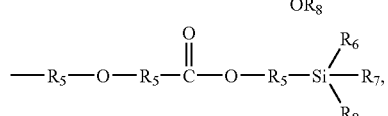
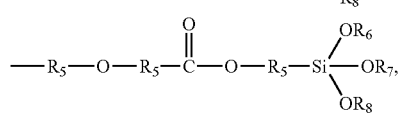
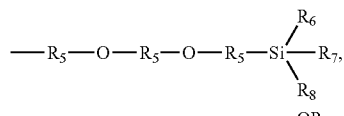
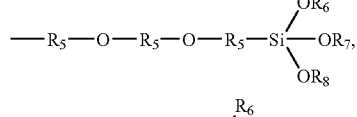
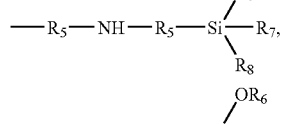
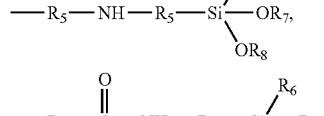
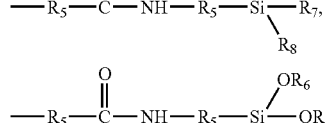
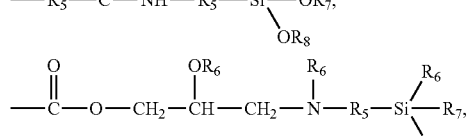
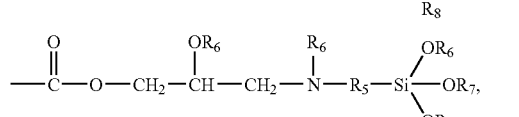
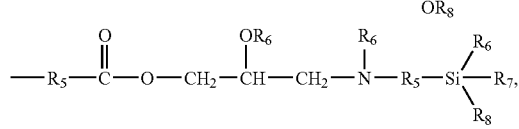

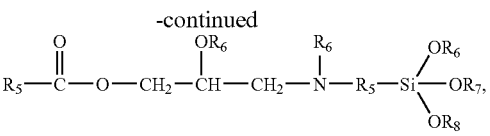
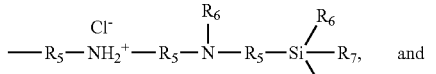
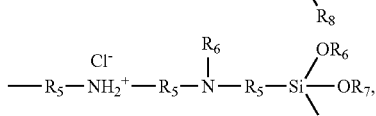

where $R_5$ is selected from the a group consisting of a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, and a substituted or unsubstituted C2-C20 alkynyl, and $R_6$, $R_7$, and $R_8$ are each independently hydrogen, halogen, a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, or a substituted or unsubstituted C2-C20 alkynyl, and

 (1a)

 (1b)

 (1c)

 (1d)

where A is a substituted or unsubstituted C1-C20 alkylene group, carbonyl, carboxy, a substituted or unsubstituted C6-C40 arylene group; B is one of oxygen, sulfur and —NH—; X is one of oxygen and sulfur; $R_9$ is a single bond the or one compound selected from a substituted or unsubstituted C1-C20 alkylene group, a substituted or unsubstituted C2-C20 alkenylene group, a substituted or unsubstituted C5-C12 cycloalkylene group, a substituted or unsubstituted C6-C40 arylene group, a substituted or unsubstituted C7-C15 aralkylene group, and a substituted or unsubstituted C2-C20 arkynylene group; and $R_{10}$, $R_{11}$, $R_{12}$, $R_{13}$, and $R_{14}$ are each independently a substituted or unsubstituted C1-C20 alkyl group, a substituted or unsubstituted C1-C20 alkoxy group, a substituted or unsubstituted C6-C30 aryloxy group, or a substituted or unsubstituted C6-C40 aryl group.

The present invention provides a polymer including a repeat unit of formula 2 below:

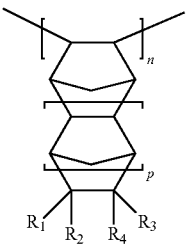

(2)

where n is an integer of 50 to 5,000, and p, $R_1$, $R_2$, $R_3$, and $R_4$ are the same as described above.

The present invention also provides a polymer including a repeat unit induced from a compound of formula 3 below:

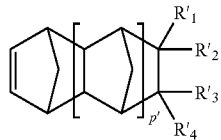

(3)

where p' is an integer of 0 to 4;

$R'_1$, $R'_2$, $R'_3$, and $R'_4$ are each independently hydrogen, halogen, a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, a substituted or unsubstituted C2-C20 alkynyl group, or a polar group selected from non-hydrocarbonaceous polar groups containing at least one of oxygen, nitrogen, phosphor, sulfur, silicon, and boron, wherein when none of $R'_1$, $R'_2$, $R'_3$, and $R'_4$ is hydrogen, halogen, or the non-hydrocarbonaceous polar group, $R'_1$ is connected to $R'_2$ or $R'_3$ is connected to $R'_4$ to form a C1-C10 alkylidene group, or $R'_1$ or $R'_2$ is connected to one of $R'_3$ and $R'_4$ to form a C4-C12 saturated or unsaturated cyclic group or a C6-C24 aromatic cyclic compound;

the non-hydrocarbonaceous polar group is selected from the a group consisting of —$OR_6$, —$OC(O)OR_6$, —$R_5OC(O)OR_6$, —$C(O)OR_6$, —$R_5C(O)OR_6$, —$C(O)R_6$, —$R_5C(O)R_6$, —$OC(O)R_6$, —$R_5OC(O)R_6$, —$(R_5O)_p$—$OR_6$, —$(OR_5)_p$—$OR_6$, —$C(O)$—$O$—$C(O)R_6$, —$R_5C(O)$—$O$—$C(O)R_6$, —$SR_6$, —$R_5SR_6$, —$SSR_6$, —$R_5SSR_6$, —$S(=O)R_6$, —$R_5S(=O)R_6$, —$R_5C(=S)R_6$, —$R_5C(=S)SR_6$, —$R_5SO_3R_6$, —$SO_3R_6$, —$R_5N=C=S$, —$NCO$, —$R_5$—$NCO$, —$CN$, —$R_5CN$, —$NNC(=S)R_6$, —$R_5NNC(=S)R_6$, —$NO_2$, —$R_5NO_2$,

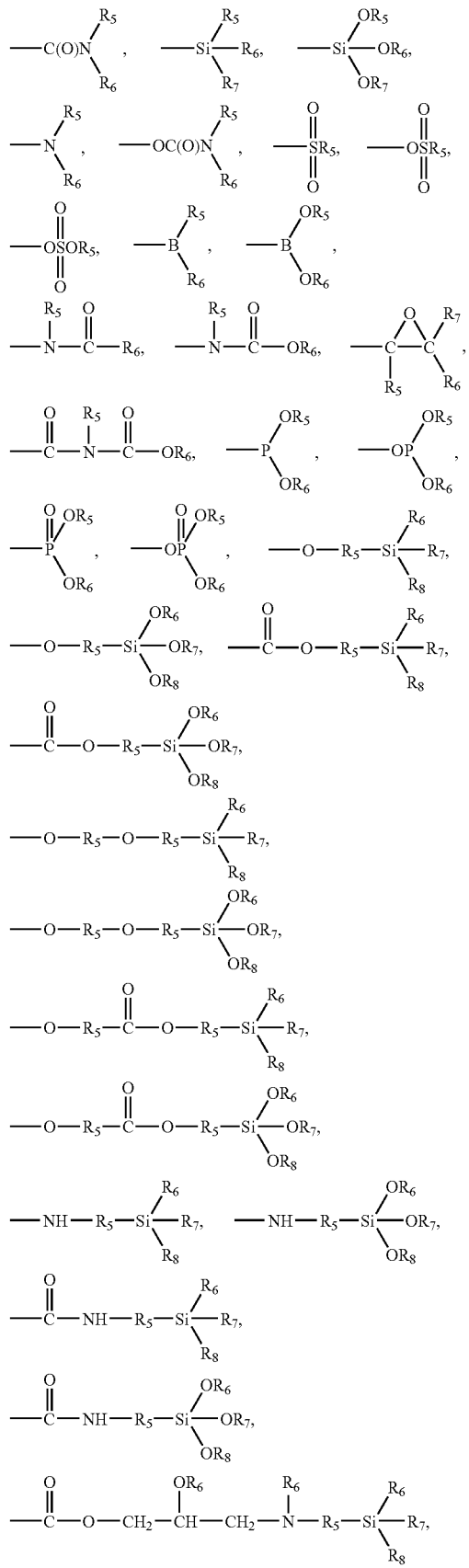

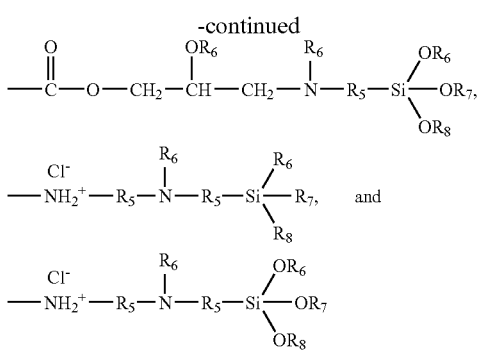

-continued where $R_5$ is selected from the a group consisting of a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, and a substituted or unsubstituted C2-C20 alkynyl, $R_6$, $R_7$, and $R_8$ are each independently hydrogen, halogen, a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, or a substituted or unsubstituted C2-C20, and p is an integer of 1 to 10.

Examples of the repeat unit induced from a compound of formula 3 include a repeat unit of formula 3a obtained through addition of a double bond, and a repeat unit of formula 3b obtained through ring opening:

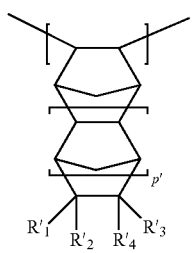

(3a)

where p', $R'_1$, $R'_2$, $R'_3$, and $R'_4$ are already described above, and

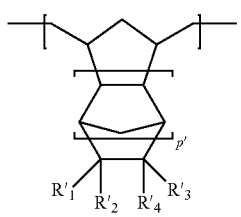

(3b)

where p', $R'_1$, $R'_2$, $R'_3$, and $R'_4$ are already described above.

When the polymer according to an embodiment of the present invention includes the repeat unit of formula 2 and the repeat unit induced from the compound of formula 3, the amount of the repeat unit of formula 2 may be in the range of 1 to 99 mol %, the repeat unit induced from the compound of formula 3 may be in the range of 1 to 99 mol %, and a degree of polymerization of the polymer may be in the range of 50 to 5000.

When the repeat unit induced from the compound of formula 3 is less than 1 mol %, solubility of the polymer decreases. On the other hand, when the repeat unit induced from the compound of formula 3 is greater than 90 mol %, the amount of the photoreactive functional group is relatively small and thus the photoreaction speed decreases.

The polymer according to an embodiment of the present invention may further include at least one repeat unit induced from the compound of formula 3, and at least one repeat unit induced from a linear olefin.

The linear olefin may be selected from a C1-C20 α-olefin, butadiene, and pentadiene.

The polymer according to an embodiment of the present invention used to form a liquid crystal alignment layer can be prepared by ring-opening polymerizing the multicyclic compound of formula 1. Such a polymer may include a repeat unit of formula 4 below.

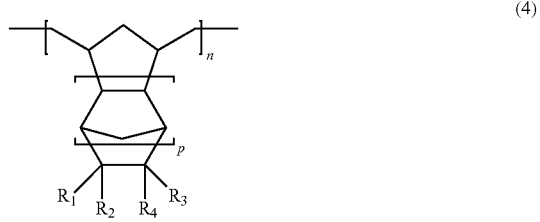

(4)

where n is an integer of 50 to 5,000, and p, $R_1$, $R_2$, $R_3$, and $R_4$ are already described above.

The polymer including the repeat unit of formula 4 may further include the repeat unit induced from the compound of formula 3, like the polymer including the repeat unit of formula 2. Particularly, the polymer may include 1 to 99 mol % of the repeat unit of formula 4 and 1 to 99 mol % of the repeat unit induced from the compound of formula 3, and a degree of polymerization of the polymer may be in the range of 50 to 5000.

The polymer including the repeat unit of formula 4 may further include at least one repeat unit induced from the compound of formula 3, and at least one repeat unit induced from a linear olefin.

The linear olefin may be selected from a C1-C20 α-olefin, butadiene, and pentadiene.

A polymer of the multi-cyclicmulticyclic compound including a photoactive group can be prepared by polymerization at 10° C. to 200° C. in the presence of a catalyst mixture including: a procatalyst containing a Group 10 transition metal; and a cocatalyst capable of weakly coordinately bonding to the transition metal of the procatalyst.

When the polymerization temperature is less than 10° C., the polymerization activity noticeably decreases. When the polymerization temperature is greater than 200° C., the catalyst mixture decomposes.

The catalyst mixture includes 1-1000 mol of the cocatalyst capable of weakly coordinately bonding to the transition metal of the procatalyst, based on 1 mol of the procatalyst containing a Group 10 transition metal. When the amount of the cocatalyst is less than 1 mol, catalyst activation is not realized. When the amount of the cocatalyst is greater than 1000 mol, the catalyst activation decreases.

The catalyst mixture may further include a compound containing a neutral Group 15 electron donor ligand.

The amount of the compound containing a neutral Group 15 electron donor ligand may be in the range of 1 to 1000 mol based on 1 mol of the procatalyst. When the amount of the compound containing a neutral Group 15 electron donor ligand is less than 1 mol, the procatalyst is less activated. On the other hand, when amount of the compound containing a neutral Group 15 electron donor ligand is greater than 1000 mol, a polymerization product yield and a molecular weight of the polymer decreases.

Examples of the procatalyst include allylpalladium chloride dimer [(Allyl)Pd(Cl)]$_2$, palladium(II)acetate [(CH$_3$CO$_2$)$_2$Pd], palladium(II)acetylacetonate [(CH3COCH=C(O—)CH$_3$)$_2$Pd], NiBr(NP(CH$_3$)$_3$)$_4$, and [PdCl(NB)O(CH$_3$)]$_2$.

The cocatalyst may be a compound that easily reacts with a lewisLewis base to produce a vacant site in a transition metal and also weakly coordinately bound to the transition metal to stabilize the generated transition metal, or a compound providing such a compound. Examples of the cocatalyst include a borane, such as B(C$_6$F$_5$)$_3$; a borate, such as dimethylanilinium tetrakis(pentafluorophenyl)borate or tricyclohexylphosphonium tetrakispentafluoropenyl borate; alkylaluminum, such as methylaluminoxane (MAO) or triethylaluminum [Al(C$_2$H$_5$)$_3$]; and a transition metal halide, such as AgSbF$_6$.

The compound including a neutral Group 15 electron donor ligand may be represented by formula 5 below:

[P(R)$_3$]                                              (5)

where R is hydrogen, a substituted or unsubstituted C1-C20 alkyl group, a substituted or unsubstituted C1-C20 alkoxy group, a substituted or unsubstituted C3-C20 allyl group, a substituted or unsubstituted C1-C20 alkenyl group, or a substituted or unsubstituted C2-C20 vinyl group; a substituted or unsubstituted C3-C12 cycloalkyl group, a substituted or unsubstituted C6-C40 aryl group, a substituted or unsubstituted C7-C15 aralkyl, or a substituted or unsubstituted C3-C20 alkynyl, wherein each of the substitutents is halogen or a C1-C20 haloalkyl group.

In particular, the compound including a neutral Group 15 electron donor ligand may be selected from tricyclohexyl phosphine, triisopropyl phosphine, tryphenyl phosphine, tri-t-butyl phosphine, or dicyclohexyl-t-butyl phosphine.

According to an embodiment of the present invention, a catalyst mixture including a procatalyst containing a Group 10 transition metal, a cocatalyst capable of weakly coordinately bonding to the transition metal of the procatalyst; and optionally a compound which includes a neutral Group 15 electron donor ligand, is prepared. Then, a monomer solution containing a norbornene-based compound including a polar functional group is subjected to additional polymerization in the presence of an organic solvent and the catalyst mixture. In this case, the sequence of adding addition of the catalyst, a monomer, and a solvent is not limited.

A photoreactive polymer solution according to an the current embodiment of the present invention is doped on a substrate including a transparent electrode and a solvent contained in the photoreactive polymer solution is removed to form a layer. Then, polarized ultraviolet rays that are polarized in a predetermined direction are irradiated on the layer so that the layer has an anisotropic characteristic.

Definition of the substituents described above will now be described in detail.

The term "alkyl group" refers to a linear or branched saturated mono-valentmonovalent hydrocarbon of 1-20 carbons, preferably 1-10 carbons, and more preferably 1-6 carbons. The alkyl group can be substituted with at least one halogen substituent. Examples of the alkyl group include methyl, ethyl, propyl, 2-propyl, n-butyl, iso-butyl, tert-butyl, pentyl, hexyl, dodecyl, fluoromethyl, difluoromethyl, trifluoromethyl, chloromethyl, dichloromethyl, trichloromethyl, iodomethyl, bromomethyl, and the like.

The term "alkenyl group" refers to a linear or branched mono-valentmonovalent hydrocarbon including at least one C—C double bond of 2-20 carbons, preferably 2-10 carbons, and more preferably 2-6 carbons. The alkenyl group can be bonded through a carbon atom including a C—C double bond or a saturated carbon atom. The alkenyl group can be substituted with at least one halogen substituent. Examples of the alkenyl group include ethenyl, 1-prophenyl, 2-prophenyl, 2-butenyl, 3-butenyl, pentenyl, 5-hexenyl, dodecenyl, and the like.

The term "cyclo alkyl group" refers to a saturated or unsaturated non-aromatic mono-valentmonovalent monocyclic, bicyclic, or tricyclic hydrocarbon of 5-12 cyclic carbons. The cyclo alkyl group can be substituted with at least one halogen substituent. Examples of the cyclo alkyl group include cyclopropyl, cyclobutyl, cyclopenty, cyclopentenyl, cyclohexyl, cyclohexenyl, cycloheptyl, cyclooctyl, decahydronaphtalenyl, adamantly, norbonyl such as bicyclo [2.2.1]hept-5-enyl, and the like.

The term "aryl group" refers to a mono-valentmonovalent monocyclic, bicyclic, or a tricyclic aromatic hydrocarbon having 6-20, for example, 6-12 carbons. The aryl group can be substituted with at least one halogen substituent. The aromatic portion of the aryl group includes only carbon atoms. Examples of the aryl group include phenyl, naphthalenyl, and fluorenyl.

The term "aralkyl group" refers to a group in which at least one hydrogen atom of the alkyl group defined above is substituted with an aryl group. The aralkyl group can be substituted with at least one halogen substituent. Examples of the aralkyl group include benzyl, benzhydril, trityl, and the like.

The term "alkynyl group" refers to a linear or branched mono-valentmonovalent hydrocharbon including at least one C—C triple bond of 2-20 carbons, preferably 2-10 carbons, and more preferably 2-6 carbons. The alkyl group can be bonded through a carbon atom including a C—C triple bond or a saturated carbon atom. The alkyl group can be substituted with at least one halogen substituent. Examples of the alkynyl group include ethynyl, propynyl, and the like.

The term "alkylene group" refers to a linear or branched saturated bi-valentbivalent hydrocarbon of 1-20 carbons, preferably 1-10 carbons, and more preferably 1-6 carbons. The alkylene group can be substituted with at least one halogen substituent. Examples of the alkyl group include methylene, ethylene, propylene, butylene, hexylene, and the like.

The term "alkenylene group" refers to a linear or branched bi-valentbivalent hydrocarbon of 2-20 carbons, preferably 2-10 carbons, and more preferably 2-6 carbons. The alkenylene group can be bonded through a carbon atom including a C—C double bond and/or a saturated carbon atom. The alkenylene group can be substituted with at least one halogen substituent.

The term "cycloalkylene" refers to a saturated or unsaturated non-aromatic bi-valentbivalent monocyclic, bicyclic, or tricyclic hydrocarbon of 5-12 cyclic carbons. The cycloalkylene can be substituted with at least one halogen substituent. Examples of the cycloalkylene include cyclopropylene, cyclobutylene, and the like.

The term "arylene group" refers to a bi-valentbivalent monocyclic, bicyclic, or tricyclic aromatic hydrocarbon of 6-20, for example, 6-12 carbons. The arylene group can be substituted with at least one halogen substituent. The aromatic portion of the arylene group includes only carbon atoms. Examples of the arylene group include phenilene and the like.

The term "aralkylene group" refers to a bi-valentbivalent hydrocarbon in which at least one hydrogen atom of the alkyl group described above is substituted with an aryl group. The aralkylene group can be substituted with at least one halogen substituent. For example, examples of the aralkylene group include benzylene and the like.

The term "arkynylene group" refers to a linear or branched bi-valentbivalent hydrocarbon including at least one C—C triple bond of 2-20 carbon atoms, preferably 2-10 carbon atoms, and more preferably 2-6 carbon atoms. The arkynylene group may be bonded through a carbon atom including a C—C triple bond or a saturated carbon atom. The arkynylene group can be substituted with at least one halogen substituent. Examples of the arkynylene group include ethynilene, propynilene, and the like.

The term "bond" refers to a simple bond to which any substituent is not added.

The present invention will be described in further detail with reference to the following examples. These examples are for illustrative purposes only and are not intended to limit the scope of the present invention.

During the following experiments, compounds sensitive to air or water were treated using a standard SchlenkSchlenk technique or a dry box technique. A nuclear magnetic resonance (NMR) spectrum was obtained using a Bruker 300 spectrometer, $^1$H NMR was measured at 300 MHz, and $^{13}$C NMR was measured at 75 MHz. The molecular weight and the distribution thereof were measured using a gel permeation chromatography (GPC) and a polystyrene sample was used as a reference.

Toluene was refined by being distilled using potassium and benzophenone, and dichloromethane was refined by being distilled using $CaH_2$.

EXAMPLE 1

Synthesis of 5-norbornene-2-methanol 397 g (3 mol) of dicyclopentadiene (DCPD) (produced from Aldrich Inc.) and 331 g (5.7 mol) of allyl alcohol (produced from Aldrich Inc.) were added to a 2 L high-pressure reactor and the temperature of the 2 L high-pressure reactor was increased to 210° C. The resulting mixture was reacted for one hour, stirring at 300 rpm. When the reaction was completed, the reactant was cooled and loaded into a distillation device. The reactant was distilled twice at a reduced pressure of 1 torr using a vacuum pump to attain a product at 56° C. (Yield: 52%).

1H-NMR (300 MHz, CDCl3): δ 6.17~5.91 (m, 2H), 3.71~3.19 (m, 2H), 2.91~2.75 (m, 2H), 2.38 (m, 1H), 1.83 (m, 1H), 1.60~1.12 (m, 2H), 0.52 (m, 1H)

EXAMPLE 2

Synthesis of 5-norbornene-2-methylcinnamate 15 g (0.121 mol) of the 5-norbornene-2-methanol prepared in Example 1, 61.2 g (0.605 mol) of triethylamine (produced from Aldrich Inc.), and 20 ml of THF were loaded into a 250 ml 2-neck flask and then stirred at 0° C. in an ice-water bath. 22.1 g (0.133 mol) of cinamoil chloride dissolved in 60 ml of THF was slowly added to the prepared mixture using an additional flask for 10 minutes. Then, the temperature of the reactant was increased to room temperature and then stirred for one hour. The resulting solution was diluted using an ethyl acetate. The diluted solution was loaded into a separatory funnel, washed using water and $NaHCO_3$ several times, and then distilled in at a reduced pressure to remove a solvent. The result was refined using a column chromatography (Hexane:Ethyl acetate=20:1) to attain a product. (Yield: 88%)

1H-NMR (300 MHz, CDCl3): δ 7.71~7.66 (dd, 1H), 7.53~7.36 (m, 5H), 6.49~6.42 (dd, 1H), 6.17~5.98 (m, 2H), 4.10~3.76 (m, 2H), 2.94~2.75 (m, 2H), 2.45 (m, 1H), 1.91~1.83 (m, 1H), 1.48~1.16 (m, 2H), 0.59 (m, 1H)

EXAMPLE 3

Polymerization of 5-norbornene-2-methylcinnamate 5 g (19.66 mmol) of 5-norbornene-2-methylcinnamate as a monomer and 5 ml of toluene refined using a solvent were loaded into a 250 ml schlenk Schlenk flask. 0.88 mg of $(CH_3CO_2)_2Pd$ and 1.1 mg of tricyclohexylphosphine dissolved in 1 ml of dichloromethane, and 6.3 mg of dimethylanilinium tetrakiss(pentafluorophenyl)borate were loaded into the flask and reacted by stirring for at 40° C. for 18 hours.

Then, the reactant was added to an excess amount of ethanol so that a white polymer precipitated. The precipitates were filtered using a glass funnel and the polymer collected. The polymer was dried in a vacuum oven at 65° C. for 24 hours. As a result, 1.6 g of a norbornene methylcinnamate polymer was attained (Mw=703,000, PDI=2.0, and Yield=32%).

EXAMPLE 4

Synthesis of 4-hydroxy methylcinnamate 20 g (0.122 mol) of 4-hydroxy cinnamic acid (produced from Aldrich Inc.) was melted in 120 ml of methanol and then 2 ml of a sulfuric acid was added thereto. The resulting mixture was refluxed at 65° C. for 5 hours. The reactant was cooled and then subjected to a reduced pressure so that an excess amount of remaining methanol was removed and a red solid was produced. The red solid was extracted using an excess amount of ethyl acetate. The extracted result was washed using $NaHCO_3$, and $H_2O$, dried over anhydrous $MgSO_4$, and then filtered. The solvent was removed using a rotary evaporator to produce a red solid product. Yield: 20.63 g (95%)

1H-NMR (400 MHz, Acetone d6): δ 7.58~7.62 (d, 1H), 7.53~7.55 (dd, 2H), 6.88~6.91 (dd, 2H), 6.32~6.36 (d, 1H), 3.70 (s, 3H)

EXAMPLE 5

Synthesis of (methyl cinnamate)-5-norbornene-2-carboxylate 11 g (79.64 mmol) of norbornene carboxylic acid (produced from Aldrich Inc.), 12.9 g (72.4 mmol) of 4-hydroxy methylcinnamate prepared according to Example 4, 22.2 g (115.84 mmol) of 1-(3-dimethylaminopropyl)-3-ethylcarbodiimide hydrochloride (EDC) (produced from Aldrich Inc.), and 14.7 g (108.6 mmol) of 1-hydroxybenzotriazole hydrate (HOBT) (produced from Aldrich Inc.) were dissolved in 100 ml of DMF in a 250 ml 2-neck flask. The temperature of the resulting solution was decreased to 0° C. and then 50 ml (362 mmol) of triethylamine was slowly dropped thereto. The temperature of the resulting solution was increased to room temperature and then the a reaction was performed for 3 hours. After the reaction was completed, the result was extracted using an excess amount of ethyl acetate. The extract was washed using NaHCO$_3$ and H$_2$O, dried over anhydrous MgSO$_4$, and then filtered. The solvent of the filtrate was removed using a rotary evaporator to produce a yellow solid product, which was refined using a column chromatography (Hexane:Ethyl acetate=6:1) to attain a pure product. (Yield: 60%)

1H-NMR (300 MHz, CDCl3): δ 7.64~7.69 (dd, 1H), 7.50~7.53 (dd, 2H), 7.05~7.14 (dd, 2H), 6.36~6.43 (dd, 1H), 6.06~6.27 (m, 2H), 3.80 (s, 3H), 2.99~3.39 (m, 3H), 2.01 (m, 1H), 1.35~1.60 (m, 3H)

EXAMPLE 6

Polymerization of (methyl cinnamate)-5-norbonene-2-carboxylate 3 g (10.06 mmol) of (methyl cinnamate)-5-norbornene-2-carboxylate as a monomer and 7 ml of a refined toluene as a solvent were loaded into a 250 ml schlenkSchlenk flask. 0.98 mg of (CH$_3$CO$_2$)$_2$Pd and 1.13 mg of tricyclohexylphosphine dissolved in 1 ml of dichloromethane, and 6.4 mg of dimethylanilinium tetrakis(pentafluorophenyl)borate were added to the flask and stirred at 90° C. for 5 hours.

Then, an excess amount of ethanol was added to the reactant to produce a white polymer precipitate. The precipitate-containing solution was, which was filteredfiltered using a glass funnel to collect the white polymer precipitate. The collected polymer was dried at 65° C. in a vacuum oven for 24 hours to produce 1.36 g of (methyl cinnamate)-5-norbornene-2-carboxylate polymer (Mw=289,000, PDI=2.76, Yield=45%).

EXAMPLE 7

Synthesis of 6-(4-oxy methyl cinnamate)hexanol 8 g (44.9 mmol) of 4-hydroxy methylcinnamate prepared according to Example 4, 2.4 g (44.9 mmol) of NaOCH$_3$ (produced from Aldrich Inc.), and 270 mg of NaI were dissolved in 100 ml of dimethylacetamide in a 250 ml 2-neck flask and stirred for one hour. Then, 6 ml (44.9 mmol) of chlorohexanol (produced from Aldrich Inc.) was added to the flask and refluxed at 100° C. for 2 days. When the reaction was completed, the reactant was cooled to room temperature and the solvent was removed. The generated solid was dissolved in an excess amount of methanol and then the non-dissolved solid was removed. The resulting solution was subjected to a reduced pressure and the solvent was removed. As a result, a white solid product was obtained (Yield: 8.4 g (67.2%))

1H-NMR (400 MHz, CDCl3): δ 7.64~7.68 (d, 1H), 7.48~7.49 (dd, 2H), 6.89~6.91 (dd, 2H), 6.30~6.34 (d, 1H), 3.98~4.02 (t, 2H), 3.81 (s, 3H), 3.67~3.70 (t, 2H), 1.46~1.84 (m, 8H)

EXAMPLE 8

Synthesis of 6-(4-oxy methyl cinnamate)hexyl-5-norbornene-2-carboxylate 5 g (36.22 mmol) of norbornene carboxylic acid (produced from Aldrich Inc.), 8.4 g (30.18 mmol) of 6-(4-oxy methyl cinnamate)hexanol prepared according to Example 7, 9.26 g (48.29 mmol) of EDC (produced from Aldrich Inc.), and 6.12 g (45.27 mmol) of HOBT (produced from Aldrich Inc.) were dissolved in 70 ml of DMF in a 250 ml 2-neck flask. The temperature of the resulting solution was decreased to 0° C. and then 21 ml (150.9 mmol) of triethylamine was slowly dropped thereto. The temperature of the resulting solution was increased to room temperature and then the a reaction was performed over nightovernight. After the reaction was completed, the result was extracted using an excess amount of ethyl acetate. The extract was washed using NaHCO$_3$ and H$_2$O, dried over anhydrous MgSO$_4$, and then filtered. The solvent of the filtrate was removed using a rotary evaporator to produce a yellow liquid product, which was refined using a column chromatography process (Hexane:Ethyl acetate=7:1) to attain a pure product. (Yield: 70%)

1H-NMR (400 MHz, CDCl3): δ 7.65~7.69 (d, 1H), 7.47~7.49 (dd, 2H), 6.90~6.92 (dd, 2H), 6.31~6.35 (d, 1H), 5.93~6.22 (m, 2H), 3.99~4.05 (tt, 4H), 3.81 (s, 3H), 2.92~3.22 (m, 3H), 2.19 (m, 1H), 1.28~1.85 (m, 11. H)

EXAMPLE 9

Polymerization of 6-(4-oxy methyl cinnamate)hexyl-5-norbornene-2-carboxylate 5 g (12.55 mmol) of 6-(4-oxy methyl cinnamate)hexyl-5-norbornene-2-carboxylate as a monomer and 5 ml of a refined toluene as a solvent were loaded into a 250 ml schlenk-Schlenk flask. 5.6 mg of (CH$_3$CO$_2$)$_2$Pd and 7 mg of tricyclohexylphosphine dissolved in 2 ml of dichloromethane, and 40.2 mg of dimethylanilinium tetrakis(pentafluorophenyl)borate were added to the flask and stirred at 90° C. for 18 hours.

Then, an excess amount of ethanol was added to the reactant to produce a white polymer precipitate. The precipitate-containing solution was, which was filteredfiltered using a glass funnel to collect the white polymer precipitate. The collected polymer was dried at 65° C. in a vacuum oven for 24 hours to produce 1.6 g of norbornene methylcinnamate polymer (Yield: 32%).

EXAMPLE 10

Synthesis of 5-norbornene-2-chalcon ester 11 g (79.64 mmol) of norbornene acid (produced from Aldrich Inc.), 16.2 g (72.4 mmol) of 2-hydroxy chalcon, 22.2 g (115.84 mmol) of EDC (produced from Aldrich Inc.), and 14.7 g (108.6 mmol) of HOBT (produced from Aldrich Inc.) were dissolved in 100 ml of DMF in a 250 ml 2-neck flask. The temperature of the resulting solution was decreased to 0° C. and then 50 ml (362 mmol) of triethylamine (produced from Aldrich Inc.) was slowly dropped thereto. The temperature of the resulting solution was increased to room temperature and then the a reaction was performed over nightovernight. After the reaction was completed, the result was extracted using an excess amount of ethyl acetate. The extract was washed using NaHCO$_3$ and H$_2$O, dried over anhydrous MgSO$_4$, and then filtered. The solvent of the filtrate was

EXAMPLE 11

Polymerization of 5-norbornene-2-chalcon ester 4.3 g (12.5 mmol) of 5-norbornene-2-chalcon ester as a monomer and 10 ml of a refined toluene as a solvent were loaded into a 250 ml schlenkSchlenk flask. 5.6 mg of $(CH_3CO_2)_2Pd$ and 7 mg of tricyclohexylphosphine dissolved in 1 ml of dichloromethane, and 40.2 mg of dimethylanilinium tetrakis(pentafluorophenyl)borate were added to the flask and stirred at 90° C. for 18 hours.

Then, an excess amount of ethanol was added to the reactant to produce a white polymer precipitate, which by filtering the reactant was filtered using a glass funnel to collect the white polymer precipitate. The collected polymer was dried at 70° C. in a vacuum oven for 24 hours to produce 3 g of norbornene-2-chalocon ester polymer (Yield: 70%).

EXAMPLE 12

Synthesis of 5-norbornene-2-coumarin ester 11 g (79.64 mmol) of norbornene acid (produced from Aldrich Inc.), 11.7 g (72.4 mmol) of 7-hydroxy coumarin, 22.2 g (115.84 mmol) of EDC (produced from Aldrich Inc.), and 14.7 g (108.6 mmol) of HOBT (produced from Aldrich Inc.) were dissolved in 100 ml of DMF in a 250 ml 2-neck flask. The temperature of the resulting solution was decreased to 0° C. and then 50 ml (362 mmol) of triethylamine (produced from Aldrich Inc.) was slowly dropped thereto. The temperature of the resulting solution was increased to room temperature and then the reaction was performed over night. After the reaction was completed, the result was extracted using an excess amount of ethyl acetate. The extract was washed using $NaHCO_3$ and $H_2O$, dried over anhydrous $MgSO_4$, and then filtered. The solvent of the filtrate was removed using a rotary evaporator to produce a product, which was recrystallized using hexane and ethanol to attain a pure product. (Yield: 70%)

EXAMPLE 13

Polymerization of 5-norbornene-2-coumarin ester 3.5 g (12.5 mmol) of 5-norbornene-2-coumarin ester as a monomer and 7 ml of a refined toluene as a solvent were loaded into a 250 ml schlenkSchlenk flask. 5.6 mg of $(CH_3CO_2)_2Pd$ and 7 mg of tricyclohexylphosphine dissolved in 1 ml of dichloromethane, and 40.2 mg of dimethylanilinium tetrakis(pentafluorophenyl)borate were added to the flask and stirred at 90° C. for 18 hours.

Then, an excess amount of ethanol was added to the reactant to produce a white polymer precipitate. The precipitate-containing solution was, which was filteredfiltered using a glass funnel to collect the white polymer precipitate. The collected polymer was dried at 70° C. in a vacuum oven for 24 hours to produce 2 g of a norbornene-2-coumarin ester polymer (Yield: 57%).

EXAMPLE 14

Synthesis of 5-norbornene-2-maleimide ester 11 g (79.64 mmol) of norbornene acid (produced from Aldrich Inc.), 8.2 g (72.4 mmol) of N-hydroxy maleimide, 22.2 g (115.84 mmol) of EDC (produced from Aldrich Inc.), and 14.7 g (108.6 mmol) of HOBT (produced from Aldrich Inc.) were dissolved in 100 ml of DMF in a 250 ml 2-neck flask. The temperature of the resulting solution was decreased to 0° C. and then 50 ml (362 mmol) of triethylamine was slowly dropped thereto. The temperature of the resulting solution was increased to room temperature and then the a reaction was performed over nightovernight. After the reaction was completed, the result was extracted using an excess amount of ethyl acetate. The extract was washed using $NaHCO_3$ and $H_2O$, dried over anhydrous $MgSO_4$, and then filtered. The solvent of the filtrate was removed using a rotary evaporator to produce a product, which was recrystallized using hexane and ethanol to attain a pure product. (Yield: 70%)

EXAMPLE 15

Polymerization of 5-norbonene-2-maleimid ester 2.9 g (12.5 mmol) of 5-norbornene-2-maleimid ester as a monomer and 6 ml of a refined toluene as a solvent were loaded into a 250 ml schlenkSchlenk flask. 5 mg of $(CH_3CO_2)_2Pd$ and 7 mg of tricyclohexylphosphine dissolved in 0.5 ml of dichloromethane, and 40.2 mg of dimethylanilinium tetrakis(pentafluorophenyl)borate were added to the flask and stirred at 90° C. for 18 hours.

Then, an excess amount of ethanol was added to the reactant to produce a white polymer precipitate. The precipitate-containing solution was, which was filteredfiltered using a glass funnel to collect the white polymer precipitate. The collected polymer was dried at 70° C. in a vacuum oven for 24 hours to produce 1.5 g of a norbornene-2-maleimid ester polymer (Yield: 52%).

EXAMPLE 16

Polymerisation of 5-norbornene-2-methylcinnamate 5 g (19.66 mmol) of 5-norbornene-2-methylcinnamate as a monomer and 5 ml of refined toluene as a solvent were added to a 250 ml schlenk flask. 0.88 mg of $(CH_3CO_2)_2Pd$ and 7.7 mg of tricyclohexyl phosphonium (tetrakis pentafluorophenyl) borate $[(Cy)_3PH][B(C_6F_5)_4]$ dissolved in 0.5 ml of dichloromethane were added to the flask, and the contained compounds were reacted while being mixed at 90° C. for 18 hours.

Then, 100 ml of toluene was added to the flask to dilute the resulting polymer solution having high viscosity, and then an excessive amount of ethanol was added thereto to produce a white copolymer precipitate. The precipitate was collected using a glass funnel and then the collected copolymer was dried in a vacuum oven at 70° C. for 24 hours to obtain 4 g of a 5-norbornene-2-methylcinnamate polymer. The weight average molecular weight (Mw) of this polymer was 350,000 and Mw/Mn was 2.92 (Yield: 80%.)

EXAMPLE 17

Polymerization of (methylcinnamate)-5-norbornene-2-carboxylate 3 g (10.06 mmol) of (methylcinnamate)-5-norbornene-2-caroxylate as a monomer and 7 ml of refined toluene as a solvent were added to a 250 ml schlenk flask. 0.98 mg of $(CH_3CO_2)_2Pd$ and 8.38 mg of tricyclohexyl phosphonium (tetrakis pentafluorophenyl)borate$[(Cy)_3PH][B(C_6F_5)_4]$ dissolved in 1 ml of dichloromethane were added to the flask, and the contained compounds were reacted while being mixed at 100° C. for 5 hours.

Then, 100 ml of toluene was added to the flask to dilute the resulting polymer solution having high viscosity, and then an excessive amount of ethanol was added thereto to produce a white copolymer precipitate. The precipitate was collected using a glass funnel and then the collected copolymer was dried in a vacuum oven at 70° C. for 24 hours to obtain 1.36 g of a (methylcinnamate)-5-norbornene-2-caroxylate polymer (Mw=94,300, PDI=2.92, and Yield=56%).

EXAMPLE 18

Polymerization of 6-(4-oxy methylcinnamate)hexyl-5-norbornene-2-carboxylate 5 g (12.55 mmol) of 6-(4-oxy methylcinnamate)hexyl-5-norbornene-2-carboxylate as a monomer and 5 ml of refined toluene as a solvent were added to a 250 ml schlenk flask. 0.56 mg of $(CH_3CO_2)_2Pd$ and 4.79 mg of tricyclohexyl phosphonium (tetrakis pentafluorophenyl) borate $[(Cy)_3PH][B(C_6F_5)_4]$ dissolved in 2 ml of dichloromethane were added to the flask, and the contained compounds were reacted while being mixed at 90° C. for 18 hours.

Then, 100 ml of toluene was added to the flask to dilute the resulting polymer solution having high viscosity, and then an excessive amount of ethanol was added thereto to produce a white copolymer precipitate. The precipitate was collected using a glass funnel and then the collected copolymer was dried in a vacuum oven at 65° C. for 24 hours to obtain 1.4 g of a 6-(4-oxy methylcinnamate)hexyl-5-norbornene-2-carboxylate polymer (Yield: 31%).

Measurement of Thermal Stability

1. Thermogravimetric analysis (TGA)

TGA of a polymer of 5-norbornene-2-methylcinnamate prepared according to Example 3 was performed using a thermogravimetric analyzer (TGA 2950 produced from TA Instrument Inc.) in a nitrogen atmosphere while a temperature was increased by 10° C. per minute in a range of room temperature to 600° C. The results are illustrated in a curve of FIG. 1.

Referring to FIG. 1, when a the temperature was 300° C. or lower, a polymer of 5-norbornene-2-methylcinnamate was stabilized; and when a the temperature was higher than 300° C., the polymer thermally decomposed.

2. Differential Scanning Calorimetry (DSC) Analysis

DSC analysis of a polymer of 5-norbornene-2-methylcinnamate prepared according to Example 3 was performed using a DSC analyzer (DSC 2920 produced from TA Instrument Inc.) in a nitrogen atmosphere under the following conditions. The results are shown in a curve of FIG. 2.

Measurement Conditions:

equilibrium: 30° C. (3 minutes)

first heating: 30° C. to 370° C. (heating rate of 10° C./min)

first cooling: to 30° C. (cooling rate: 10° C./min)

equilibrium: −30° C. (3 minutes)

second heating: −30° C. to 370° C. (heating rate: 10° C./min)

Figure 2:
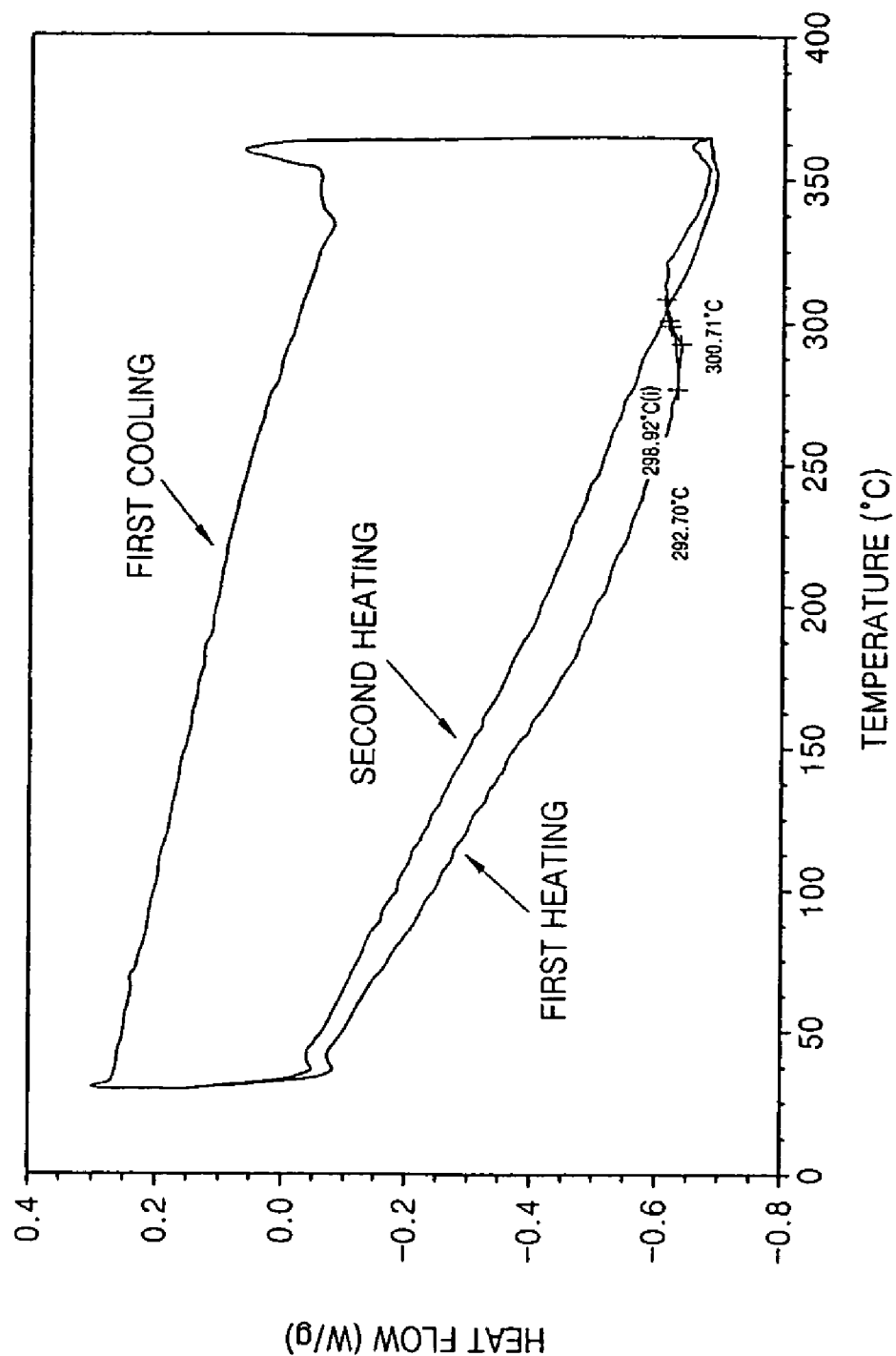
FIG. 2 shows differential scanning calorimetry analysis curves of a polymer according to Example 3.

Referring to FIG. 2, the polymer of 5-norbornene-2-methylcinnamate did not have $T_g$ in a temperature range of 30° C.-370° C.

Through the results of TGA and the DSC analysis, it was determined that a polymer of 5-norbornene-2-methylcinnamate according to an embodiment of the present invention exhibited high thermal stability at a temperature of as high as about 370° C. or less.

A photoreactive polymer according to an embodiment of the present invention exhibits a high glass transition temperature since it includes a multi-cyclicmulticyclic compound having a high glass transition temperature at as its main chain. In addition, the photoreactive polymer has a relatively large vacancy so that a photoreactive group can move relatively freely in the main chain of the polymer. As a result, a slow photoreaction rate, which is a disadvantage of a conventional polymer material used to form an alignment layer for a liquid crystal display device, can be overcome.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A polymer comprising a repeat unit of formula 2 below:

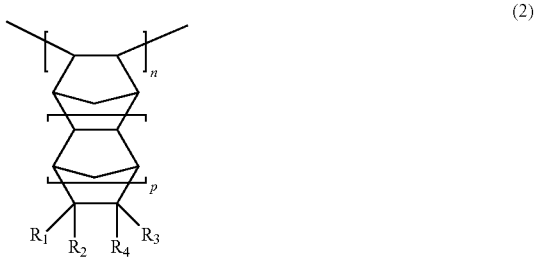

(2)

where n is an integer of 50 to 5,000;

p is an integer of 0 to 4;

at least one of $R_1$, $R_2$, $R_3$, and $R_4$ is a radical selected from a group consisting of a compound represented by formula 1a, a compound represented by formula 1b, a compound represented by formula 1c, and a compound represented by formula 1d; and the remaining three of $R_1$, $R_2$, $R_3$, and $R_4$ are each independently one of hydrogen, halogen, a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, a substituted or unsubstituted C2-C20 alkynyl group, or a polar group selected from non-hydrocarbonaceous polar groups containing at least one of oxygen, nitrogen, phosphor, sulfur, silicon, and boron, wherein when none of $R_1$, $R_2$, $R_3$, and $R_4$ is hydrogen, halogen, or the non-hydrocarbonaceous polar group, $R_1$ is connected to $R_2$ or $R_3$ is connected to $R_4$ to form a C1-C10 alkylidene group, or $R_1$ or $R_2$ is connected to one of $R_3$ and $R_4$ to form a C4-C12 saturated or unsaturated cyclic group or a C6-C24 aromatic cyclic compound, the non-hydrocarbonaceous polar group is selected from a group consisting of —$OR_6$, —$OC(O)OR_6$, —$R_5OR_6$, —$R_5OC(O)OR_6$, —$C(O)OR_6$, —$R_5C(O)OR_6$, —$C(O)R_6$, —$R_5C(O)R_6$, —$OC(O)R_6$, —$R_5OC(O)R_6$, —$(R_5O)_p$—$OR_6$, —$(OR_5)_pOR_6$, —$C(O)$—$O$—$C(O)R_6$, —$R_5C(O)$—$O$—$C(O)R_6$, —$SR_6$, —$R_5SR_6$, —$SSR_6$, —$R_5SSR_6$, —$S(=O)R_6$, —$R_5S(=O)R_6$, —$R_5C(=S)$

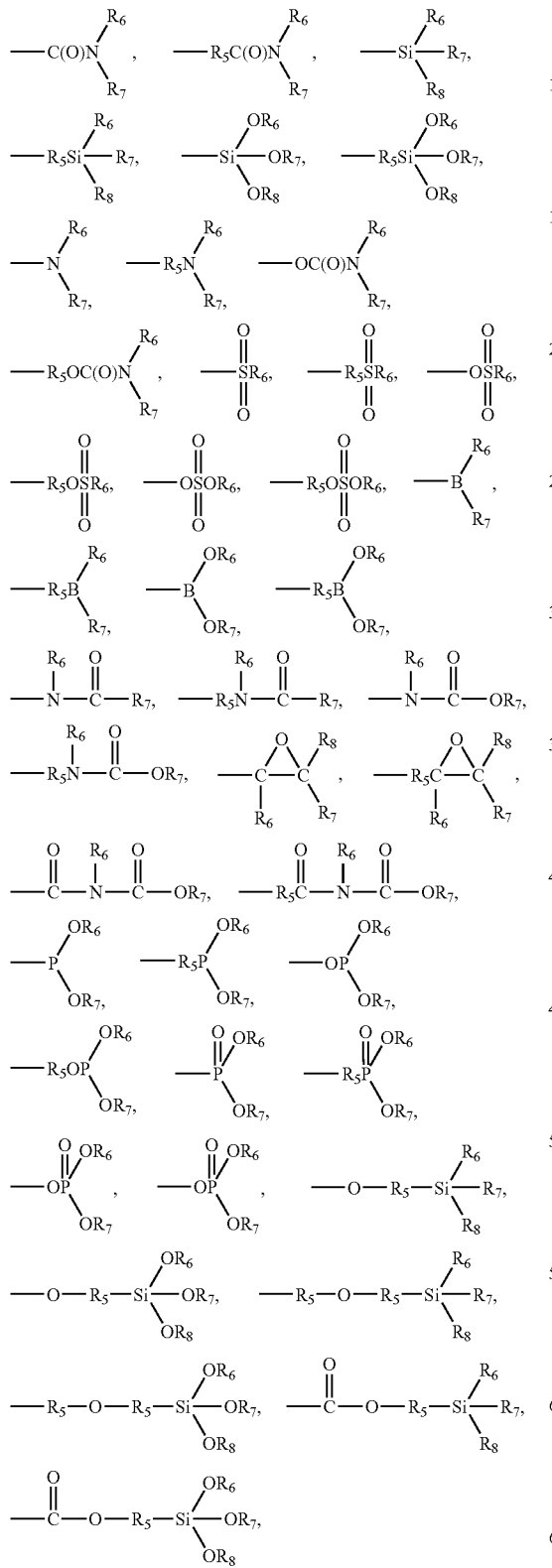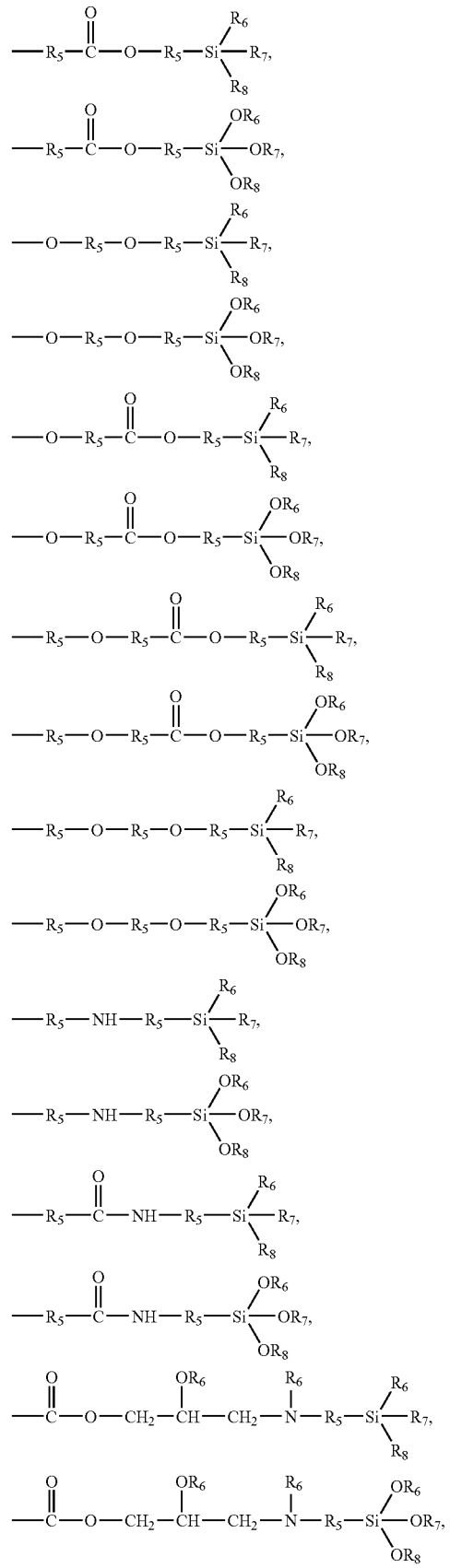

-continued

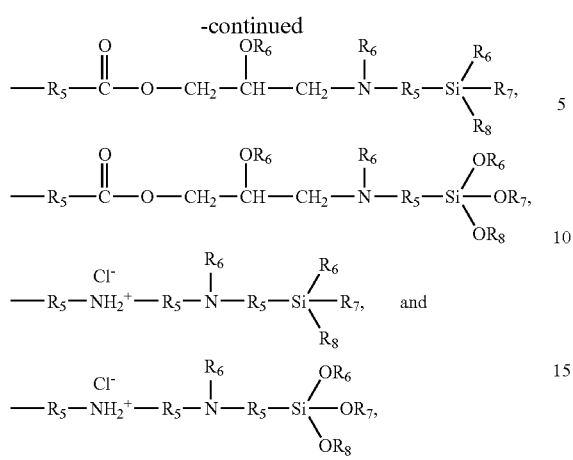

where R$_5$ is selected from a group consisting of a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, and a substituted or unsubstituted C2-C20 alkynyl, and R$_6$, R$_7$, and R$_8$ are each independently one of hydrogen, halogen, a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, or a substituted or unsubstituted C2-C20 alkynyl, and

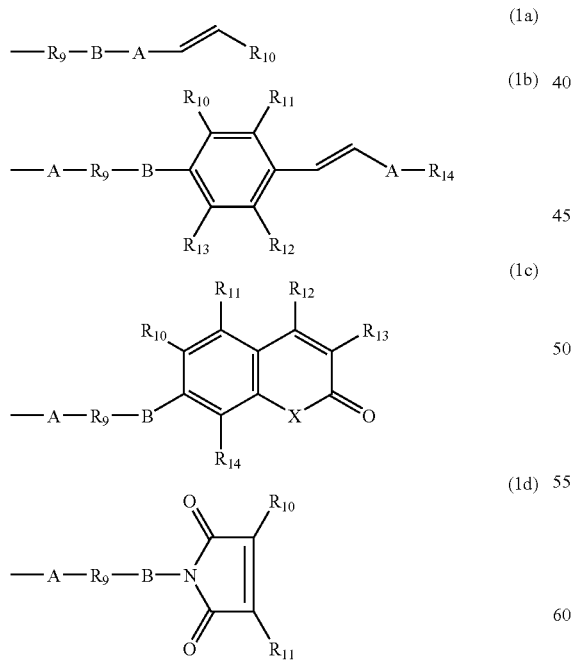

where A is a substituted or unsubstituted C1-C20 alkylene group, carbonyl, carboxy, a substituted or unsubstituted C6-C40 arylene group; B is one of oxygen, sulfur and —NH—; X is one of oxygen and sulfur; R$_9$ is a single bond or one compound selected from a group consisting of a substituted or unsubstituted C1-C20 alkylene group, a substituted or unsubstituted C2-C20 alkenylene group, a substituted or unsubstituted C5-C12 cycloalkylene group, a substituted or unsubstituted C6-C40 arylene group, a substituted or unsubstituted C7-C15 aralkylene group, or a substituted and unsubstituted C2-C20 alkylnylene group; and R$_{10}$, R$_{11}$, R$_{12}$, R$_{13}$, and R$_{14}$ are each independently one of a substituted or unsubstituted C1-C20 alkyl group, a substituted or unsubstituted C1-C20 alkoxy group, a substituted or unsubstituted C6-C30 aryloxy group, and a substituted or unsubstituted C6-C40 aryl group.

2. The polymer of claim 1, further comprising a repeat unit induced from a compound of formula 3 below:

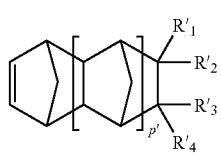

(3)

where p' is an integer of 0 to 4;

R'$_1$, R'$_2$, R'$_3$, and R'$_4$ are each independently one of hydrogen, halogen, a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, a substituted or unsubstituted C2-C20 alkynyl group, and a polar group selected from non-hydrocarbonaceous polar groups containing at least one of oxygen, nitrogen, phosphor, sulfur, silicon, and boron, wherein when none of R'$_1$, R'$_2$, R'$_3$, and R'$_4$ is hydrogen, halogen, or the non-hydrocarbonaceous polar group, R'$_1$ is connected to R'$_2$ or R'$_3$ is connected to R'$_4$ to form a C1-C10 alkylidene group, or R'$_1$ or R'$_2$ is connected to one of R'$_3$ and R'$_4$ to form a C4-C12 saturated or unsaturated cyclic group or a C6-C24 aromatic cyclic compound;

the non-hydrocarbonaceous polar group is selected from a group consisting of —OR$_6$, —OC(O)OR$_6$, —R$_5$OC(O)OR$_6$, —C(O)OR$_6$, —R$_5$C(O)OR$_6$, -C(O)R$_6$, —R$_5$C(O)R$_6$, —OC(O)R$_6$, —R$_5$OC(O)R$_6$, —(R$_5$O)$_p$—OR$_6$, —(OR$_5$)$_p$—OR$_6$, —C(O)—O—C(O)R$_6$, —R$_5$C(O)—O—C(O)R$_6$, —SR$_6$, —R$_5$SR$_6$, —SSR$_6$, —R$_5$SSR$_6$, —S(=O)R$_6$, -R$_5$S(=O)R$_6$, —R$_5$C(=S)R$_6$, —R$_5$C(=S)SR$_6$, —R$_5$SO$_3$R$_6$, —SO$_3$R$_6$, —R$_5$N=C=S, —NCO, —R$_5$—NCO, —CN, —R$_5$CN, —NNC(=S)R$_6$, —R$_5$NNC(=S)R$_6$, —NO$_2$, —R$_5$NO$_2$,

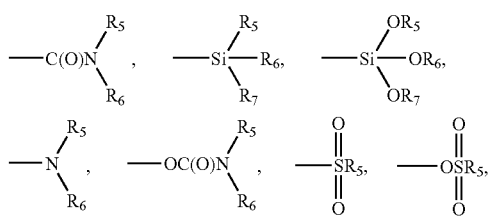

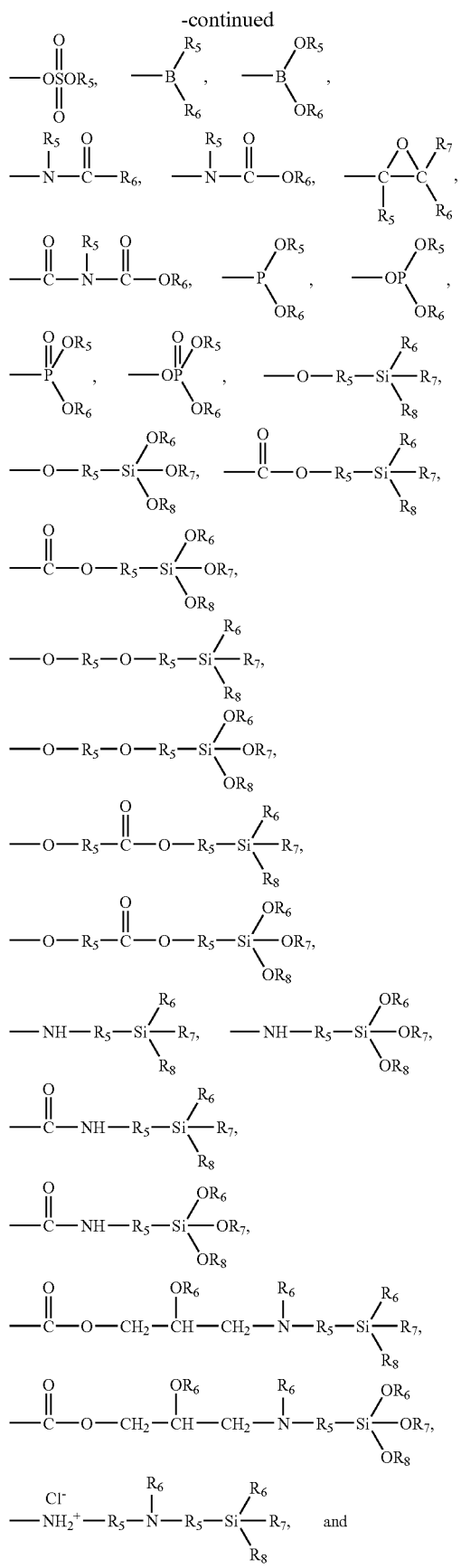

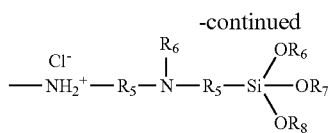

where R₅ is selected from a group consisting of a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, and a substituted or unsubstituted C2-C20 alkynyl, $R_6$, $R_7$, and $R_8$ are each independently one of hydrogen, halogen, a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, or a substituted or unsubstituted C2-C20, and p is an integer of 1 to 10.

3. The polymer of claim 2, wherein the amount of the repeat unit of formula 2 is in the range of 1 to 99% by mol and the amount of the repeat unit induced from a compound of formula 3 is in the range of 1 to 99% by mol, and a degree of polymerization is in the range of 50 to 5,000.

4. The polymer of claim 1, further comprising at least one repeat unit induced from a compound of formula 3 and at least one linear olefin:

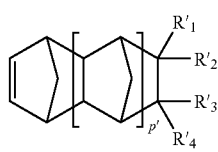

(3)

where p' is an integer of 0 to 4;

$R'_1$, $R'_2$, $R'_3$, and $R'_4$ are each independently one of hydrogen, halogen, a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, a substituted or unsubstituted C2-C20 alkynyl group, and a polar group selected from non-hydrocarbonaceous polar groups containing at least one of oxygen, nitrogen, phosphor, sulfur, silicon, and boron, wherein when none of $R'_1$, $R'_2$, $R'_3$, and $R'_4$ is hydrogen, halogen, or the non-hydrocarbonaceous polar group, $R'_1$ is connected to $R'_2$ or $R'_3$ is connected to $R'_4$ to form a C1-C10 alkylidene group, or $R'_1$ or $R'_2$ is connected to one of $R'_3$ and $R'_4$ to form a C4-C12 saturated or unsaturated cyclic group or a C6-C24 aromatic cyclic compound;

the non-hydrocarbonaceous polar group is selected from a group consisting of —OR₆, —OC(O)OR₆, —R₅OC(O)OR₆, —C(O)OR₆, —R₅C(O)OR₆, —C(O)R₆, —R₅C(O)R₆, —OC(O)R₆, —R₅OC(O)R₆, —(R₅O)ₚ—OR₆, —(OR₅)ₚ—OR₆, —C(O)—O—C(O)R₆, —R₅C(O)—O—C(O)R₆, —SR₆, —R₅SR₆, —SSR₆, —R₅SSR₆, —S(=O)R₆, —R₅S(=O)R₆, —R₅C(=S)R₆, —R₅C (=S)SR₆, —R₅SO₃R₆, —SO₃R₆, —R₅N=C=S, —NCO, —R₅—NCO, —CN, —R₅CN, —NNC(=S)R₆, —R₅NNC(=S)R₆, —NO₂, —R₅NO₂,

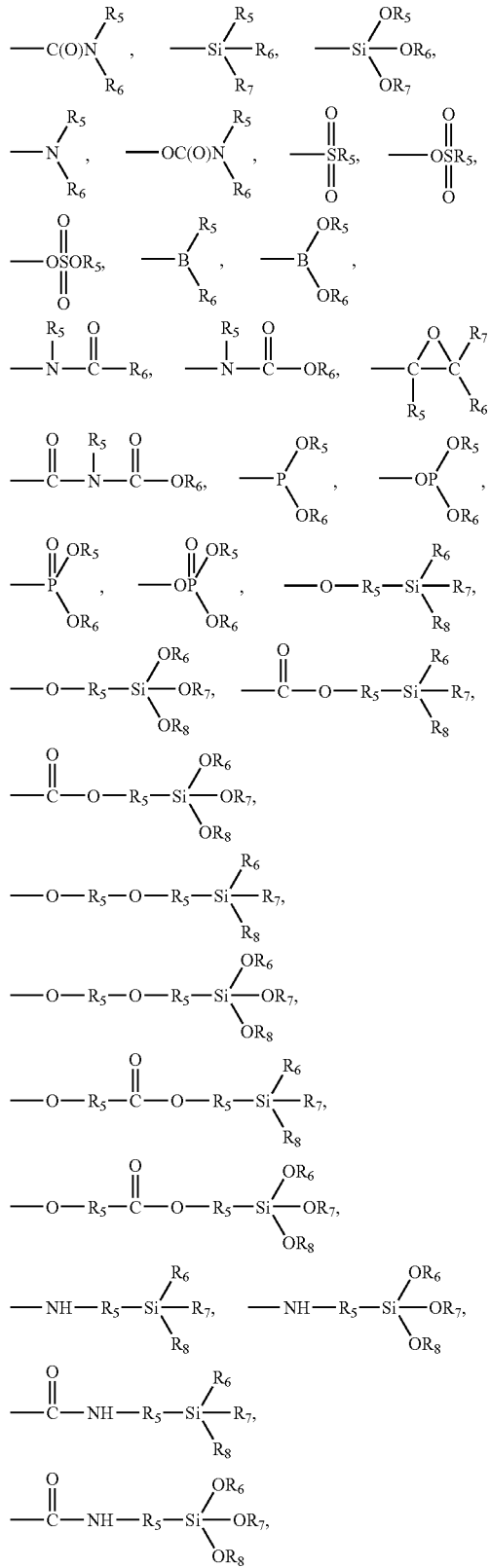

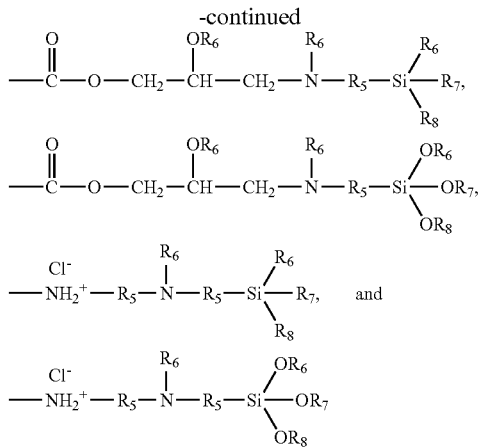

where $R_5$ is selected from a group consisting of a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, and a substituted or unsubstituted C2-C20 alkynyl, $R_6$, $R_7$, and $R_8$ are each independently one of hydrogen, halogen, a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, or a substituted or unsubstituted C2-C20, and p is an integer of 1 to 10.

5. The polymer of claim 4, wherein the linear olefin is one of C1-C20 α-olefin, butadiene, and pentadiene.

6. A polymer comprising a repeat unit of formula 4 below:

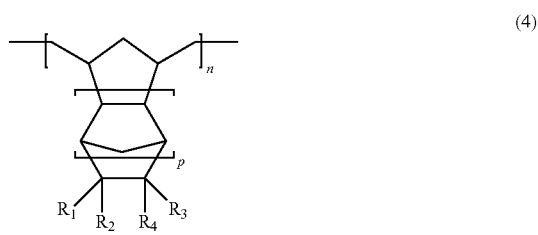

(4)

where n is an integer of 50 to 5,000;

p is an integer of 0 to 4;

at least one of $R_1$, $R_2$, $R_3$, and $R_4$ is a radical selected from a group consisting of the a compound represented by formula 1a, a compound represented by formula 1b, a compound represented by formula 1c, and a compound represented by formula 1d; and the remaining three of $R_1$, $R_2$, $R_3$, and $R_4$ are each independently one of hydrogen, halogen, a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, a substituted or unsubstituted C2-C20 alkynyl group, or a polar group selected from non-hydrocarbonaceous polar groups containing at least one of oxygen, nitrogen, phosphor, sulfur, silicon, and boron, wherein when none of $R_1$, $R_2$, $R_3$, and $R_4$ is hydrogen, halogen, or the non-hydrocarbonaceous polar group, $R_1$ is connected to $R_2$ or $R_3$ is connected to $R_4$ to form a C1-C10 alkylidene group, or $R_1$ or $R_2$ is connected to one of $R_3$ and $R_4$ to form a C4-C12 saturated or unsaturated cyclic group or a C6-C24 aromatic cyclic compound, the non-hydrocarbonaceous polar group is selected from a group consisting of —$OR_6$, —$OC(O)OR_6$, —$R_5OR_6$, —$R_5OC(O)OR_6$, —$C(O)OR_6$, —$R_5C(O)OR_6$, —$C(O)R_6$, —$R_5C(O)R_6$, —$OC(O)R_6$, —$R_5OC(O)R_6$, —$(R_5O)_p$—$OR_6$, —$(OR_5)_p$—$OR_6$, —$C(O)$—$O$—$C(O)R_6$, —$R_5C(O)$—$O$—$C(O)R_6$, —$SR_6$, —$R_5SR_6$, —$SSR_6$, —$R_5SSR_6$, —$S(=O)R_6$, —$R_5S(=O)R_6$, —$R_5C(=S)R_6$, —$R_5C(=S)SR_6$, —$R_5SO_3R_6$, —$SO_3R_6$, —$R_5N=C=S$, —NCO, $R_5$—NCO, —CN, —$R_5CN$, —$NNC(=S)R_6$, —$R_5NNC(=S)R_6$, —$NO_2$, —$R_5NO_2$, —C(O)N($R_6$)($R_7$), —$R_5$C(O)N($R_6$)($R_7$), —Si($R_6$)($R_7$)($R_8$), —$R_5$Si($R_6$)($R_7$)($R_8$), —Si($OR_6$)($OR_7$)($OR_8$), —$R_5$Si($OR_6$)($OR_7$)($OR_8$),

—N($R_6$)($R_7$), —$R_5$N($R_6$)($R_7$), —OC(O)N($R_6$)($R_7$),

—$R_5$OC(O)N($R_6$)($R_7$), —S(=O)(=O)$R_6$, —$R_5$S(=O)(=O)$R_6$, —OS(=O)(=O)$R_6$,

—$R_5$OS(=O)(=O)$R_6$, —OS(=O)(=O)$OR_6$, —$R_5$OS(=O)(=O)$OR_6$, —B($R_6$)($R_7$),

—$R_5$B($R_6$)($R_7$), —B($OR_6$)($OR_7$), —$R_5$B($OR_6$)($OR_7$),

—N($R_6$)—C(=O)$R_7$, —$R_5$N($R_6$)—C(=O)$R_7$, —N($R_6$)—C(=O)$OR_7$,

—$R_5$N($R_6$)—C(=O)$OR_7$, —C($R_6$)($R_7$)—C($R_8$)(epoxide O), —$R_5$C($R_6$)($R_7$)—C($R_8$)(epoxide O),

—C(=O)—N($R_6$)—C(=O)$OR_7$, —$R_5$C(=O)—N($R_6$)—C(=O)$OR_7$,

—P($OR_6$)($OR_7$), —$R_5$P($OR_6$)($OR_7$), —OP($OR_6$)($OR_7$),

—$R_5$OP($OR_6$)($OR_7$), —P(=O)($OR_6$)($OR_7$), —$R_5$P(=O)($OR_6$)($OR_7$),

—OP(=O)($OR_6$)($OR_7$), —OP(=O)($OR_6$)($OR_7$), —O—$R_5$—Si($R_6$)($R_7$)($R_8$),

—O—$R_5$—Si($OR_6$)($OR_7$)($OR_8$), —$R_5$—O—$R_5$—Si($R_6$)($R_7$)($R_8$),

—$R_5$—O—$R_5$—Si($OR_6$)($OR_7$)($OR_8$), —C(=O)—O—$R_5$—Si($R_6$)($R_7$)($R_8$),

—C(=O)—O—$R_5$—Si($OR_6$)($OR_7$)($OR_8$),

—$R_5$—C(=O)—O—$R_5$—Si($R_6$)($R_7$)($R_8$),

—$R_5$—C(=O)—O—$R_5$—Si($OR_6$)($OR_7$)($OR_8$),

—O—$R_5$—O—$R_5$—Si($R_6$)($R_7$)($R_8$),

—O—$R_5$—O—$R_5$—Si($OR_6$)($OR_7$)($OR_8$),

—O—$R_5$—C(=O)—O—$R_5$—Si($R_6$)($R_7$)($R_8$),

—O—$R_5$—C(=O)—O—$R_5$—Si($OR_6$)($OR_7$)($OR_8$),

—$R_5$—O—$R_5$—C(=O)—O—$R_5$—Si($R_6$)($R_7$)($R_8$),

—$R_5$—O—$R_5$—C(=O)—O—$R_5$—Si($OR_6$)($OR_7$)($OR_8$),

—$R_5$—O—$R_5$—O—$R_5$—Si($R_6$)($R_7$)($R_8$),

—$R_5$—O—$R_5$—O—$R_5$—Si($OR_6$)($OR_7$)($OR_8$),

—$R_5$—NH—$R_5$—Si($R_6$)($R_7$)($R_8$),

—$R_5$—NH—$R_5$—Si($OR_6$)($OR_7$)($OR_8$),

-continued

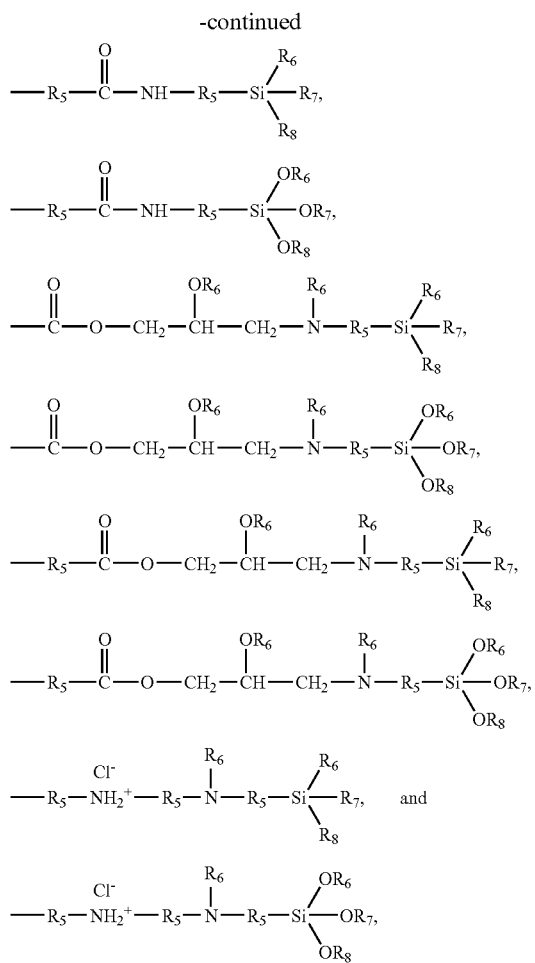

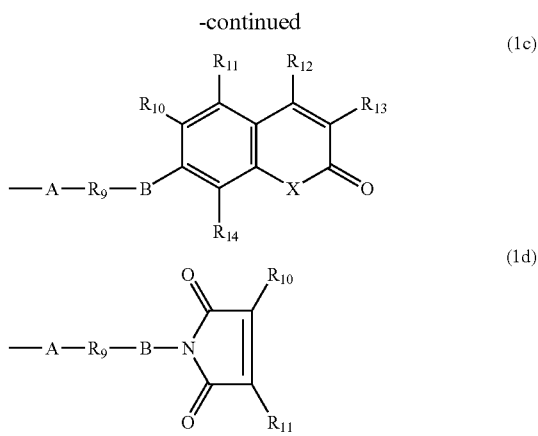

where A is a substituted or unsubstituted C1-C20 alkylene group, carbonyl, carboxy, a substituted or unsubstituted C6-C40 arylene group; B is one of oxygen, sulfur and —NH—; X is one of oxygen and sulfur; $R_9$ is a single bond or one compound selected from a group consisting of a substituted or unsubstituted C1-C20 alkylene group, a substituted or unsubstituted C2-C20 alkenylene group, a substituted or unsubstituted C5-C12 cycloalkylene group, a substituted or unsubstituted C6-C40 arylene group, a substituted or unsubstituted C7-C15 aralkylene group, or a substituted and unsubstituted C2-C20 alkylnylene group; and $R_{10}$, $R_{11}$, $R_{12}$, $R_{13}$, and $R_{14}$ are each independently one of a substituted or unsubstituted C1-C20 alkyl group, a substituted or unsubstituted C1-C20 alkoxy group, a substituted or unsubstituted C6-C30 aryloxy group, and a substituted or unsubstituted C6-C40 aryl group, except that A is carbonyl, carboxy, a substituted or unsubstituted C6-C40 arylene group in formula (1b).

7. The polymer of claim 6, further comprising a repeat unit induced from a compound of formula 3:

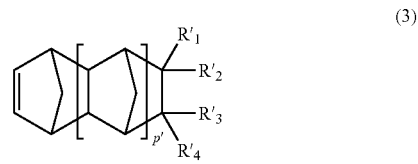

where p' is an integer of 0 to 4;

$R'_1$, $R'_2$, $R'_3$, and $R'_4$ are each independently one of hydrogen, halogen, a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, a substituted or unsubstituted C2-C20 alkynyl group, and a polar group selected from non-hydrocarbonaceous polar groups containing at least one of oxygen, nitrogen, phosphor, sulfur, silicon, and boron, wherein when none of $R'_1$, $R'_2$, $R'_3$, and $R'_4$ is hydrogen, halogen, or the non-hydrocarbonaceous polar group, $R'_1$ is connected to $R'_2$ or $R'_3$ is connected to $R'_4$ to form a C1-C10 alkylidene group, or $R'_1$ or $R'_2$ is connected to where $R_5$ is selected from a group consisting of a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, and a substituted or unsubstituted C2-C20 alkynyl, and $R_6$, $R_7$, and $R_8$ are each independently one of hydrogen, halogen, a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, and a substituted or unsubstituted C2-C20 alkynyl, and

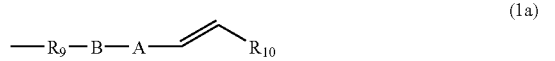

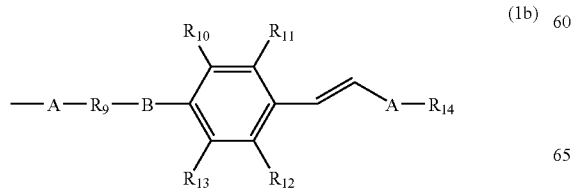

one of R'₃ and R'₄ to form a C4-C12 saturated or unsaturated cyclic group or a C6-C24 aromatic cyclic compound;

the non-hydrocarbonaceous polar group is selected from a group consisting of —OR₆, —OC(O)OR₆, —R₅OC(O)OR₆, —C(O)OR₆, —R₅C(O)OR₆, —C(O)R₆, —R₅C(O)R₆, —OC(O)R₆, —R₅OC(O)R₆, —(R₅O)ₚ—OR₆, —(OR₅)ₚ—OR₆, —C(O)—O—C(O)R₆, —R₅C(O)—O—C(O)R₆, —SR₆, —R₅SR₆, —SSR₆, —R₅SSR₆, —S(=O)R₆, —R₅S(=O)R₆, —R₅C(=S)R₆, —R₅C(=S)SR₆, —R₅SO₃R₆, —SO₃R₆, —R₅N=C=S, —NCO, —R₅—NCO, —CN, —R₅CN, —NNC(=S)R₆, —R₅NNC(=S)R₆, —NO₂, —R₅NO₂,

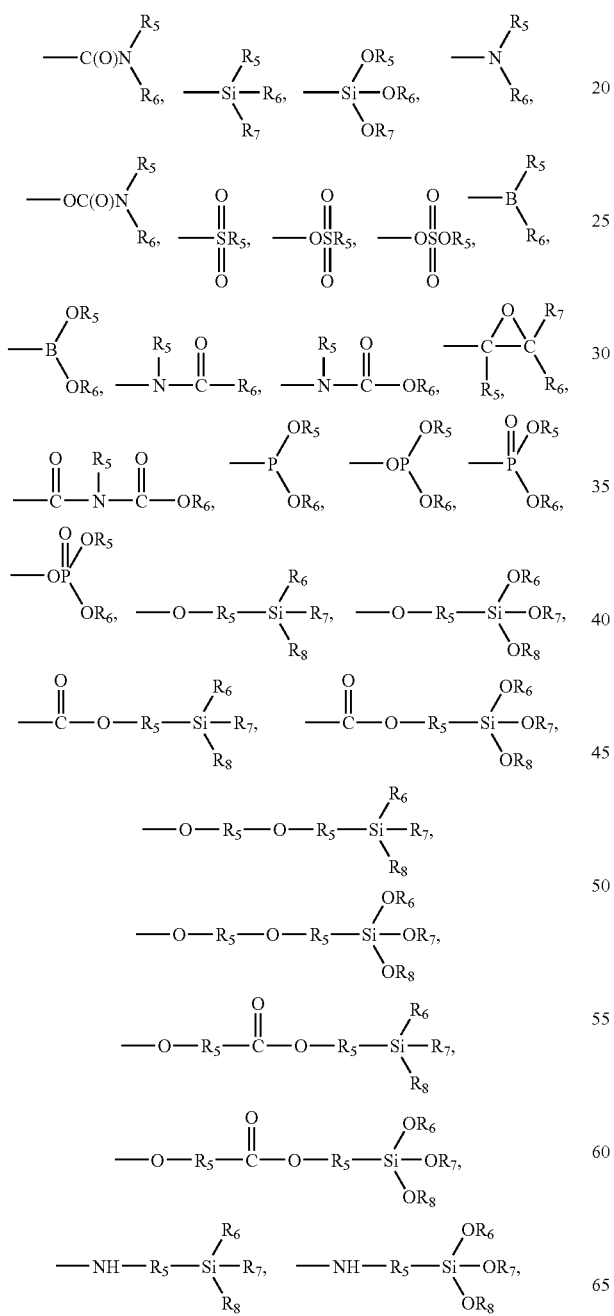

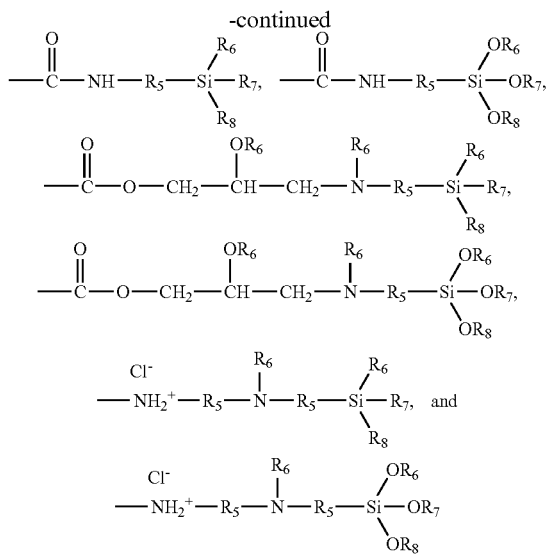

where R₅ is selected from a group consisting of a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, and a substituted or unsubstituted C2-C20 alkynyl, R₆, R₇, and R₈ are each independently one of hydrogen, halogen, a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, or a substituted or unsubstituted C2-C20, and p is an integer of 1 to 10.

8. The polymer of claim 7, wherein the amount of the repeat unit of formula 4 is in the range of 1 to 99 mol % and the amount of the repeat unit induced from a compound of formula 3 is in the range of 1 to 99 mol %, and a degree of polymerization is in the range of 50 to 5,000.

9. The polymer of claim 6, further comprising at least one repeat unit induced from a compound of formula 3 and at least one linear olefin:

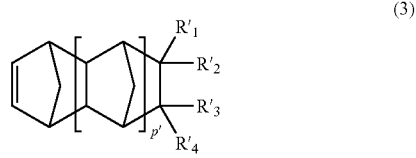

(3)

where p' is an integer of 0 to 4;

R'₁, R'₂, R'₃, and R'₄ are each independently one of hydrogen, halogen, a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, a substituted or unsubstituted C2-C20 alkynyl group, and a polar group selected from non-hydrocarbonaceous polar groups containing at least one of oxygen, nitrogen, phosphor, sulfur, silicon, and boron, wherein when none of $R'_1$, $R'_2$, $R'_3$, and $R'_4$ is hydrogen, halogen, or the non-hydrocarbonaceous polar group, $R'_1$ is connected to $R'_2$ or $R'_3$ is connected to $R'_4$ to form a C1-C10 alkylidene group, or $R'_1$ or $R'_2$ is connected to one of $R'_3$ and $R'_4$ to form a C4-C12 saturated or unsaturated cyclic group or a C6-C24 aromatic cyclic compound;

the non-hydrocarbonaceous polar group is selected from a group consisting of $-OR_6$, $-OC(O)OR_6$, $-R_5OC(O)OR_6$, $-C(O)OR_6$, $-R_5C(O)OR_6$, $-C(O)R_6$, $-R_5C(O)R_6$, $-OC(O)R_6$, $-R_5OC(O)R_6$, $-(R_5O)_p-OR_6$, $-(OR_5)_p-OR_6$, $-C(O)-O-C(O)R_6$, $-R_5C(O)-O-C(O)R_6$, $-SR_6$, $-R_5SR_6$, $-SSR_6$, $-R_5SSR_6$, $-S(=O)R_6$, $-R_5S(=O)R_6$, $-R_5C(=S)R_6$, $-R_5C(=S)SR_6$, $-R_5SO_3R_6$, $-SO_3R_6$, $-R_5N=C=S$, $-NCO$, $-R_5-NCO$, $-CN$, $-R_5CN$, $-NNC(=S)R_6$, $-R_5NNC(=S)R_6$, $-NO_2$, $-R_5NO_2$,

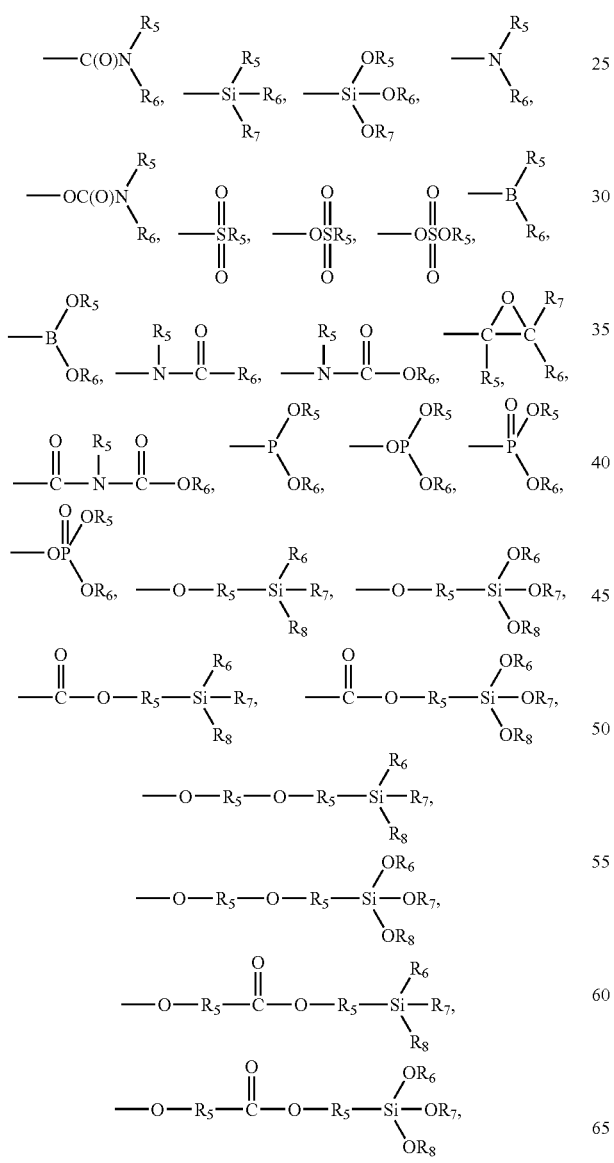

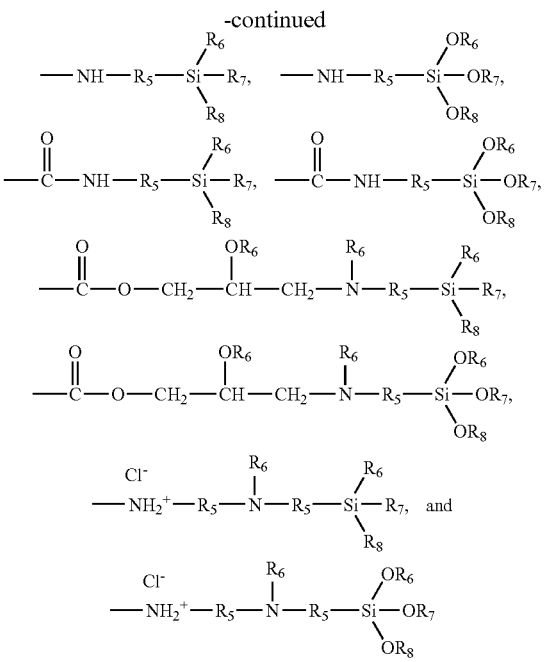

where $R_5$ is selected from a group consisting of a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, and a substituted or unsubstituted C2-C20 alkynyl, $R_6$, $R_7$, and $R_8$ are each independently one of hydrogen, halogen, a substituted or unsubstituted C1-C20 alkyl group, a substituted or unsubstituted C2-C20 alkenyl group, a substituted or unsubstituted C5-C12 cycloalkyl group, a substituted or unsubstituted C6-C40 aryl group, a substituted or unsubstituted C7-C15 aralkyl group, or a substituted or unsubstituted C2-C20, and p is an integer of 1 to 10.

10. The polymer of claim 9, wherein the linear olefin is one of C1-C20 α-olefin, butadiene, and pentadiene.

11. A method of preparing the polymer of any one of claims 1 through 10 at a temperature of 10° C. to 200° C. in the presence of a catalyst mixture of a procatalyst comprising a Group 10 transition metal and a cocatalyst capable of weakly coordinately bonding to the transition metal of the procatalyst.

12. The method of claim 11, wherein the catalyst mixture comprises 1-1000 mol of the cocatalyst based on 1 mol of the procatalyst.

13. The method of claim 11, wherein the catalyst mixture further comprises a compound containing a neutral Group 15 electron donor ligand.

14. The method of claim 13, wherein the catalyst mixture comprises 1-1000 mol of the compound containing a neutral Group 15 electron donor ligand based on 1 mol of the procatalyst.

15. The method of claim 11, wherein the procatalyst is selected from a group consisting of allylpalladium chloride dimer [(Allyl)Pd(Cl)]$_2$, palladium(II)acetate [(CH$_3$CO$_2$)$_2$Pd], palladium(II) acetylacetonate [(CH$_3$COCH=C(O-)CH$_3$)$_2$Pd], NiBr(NP(CH$_3$)$_3$)$_4$, and [PdCl(NB)O(CH$_3$)]$_2$.

16. The method of claim 11, wherein the cocatalyst is selected from a group consisting of borane, borate, alkylaluminum, alkyl aluminoxane, and a transition metal halide.

17. The method of claim 13, wherein the compound containing a neutral Group 15 electron donor ligand is represented by formula 5 below:

$$[P(R)3] \quad (5)$$

where R is hydrogen, a substituted or unsubstituted C1-C20 alkyl group, a substituted or unsubstituted C1-C20 alkoxy group, a substituted or unsubstituted C3-C20 allyl group, a substituted or unsubstituted C1-C20 alkenyl group, or a substituted or unsubstituted C2-C20 vinyl group; a substituted or unsubstituted C3-C12 cycloalkyl group, a substituted or unsubstituted C6-C40 aryl group, a substituted or unsubstituted C7-C15 aralkyl, or a substituted or unsubstituted C3-C20 alkynyl, wherein each of the substitutents is halogen or a C1-C20 haloalkyl group.

18. The method of claim 13, wherein the compound containing a neutral Group 15 electron donor ligand is selected from the group consisting of tricyclohexyl phosphine, triisopropyl phosphine, tryphenyl phosphine, tri-t-butyl phosphine, and dicyclohexyl-t-butyl phosphine.

* * * * *